(12) United States Patent
Jayaram et al.

(10) Patent No.: US 11,146,511 B1
(45) Date of Patent: Oct. 12, 2021

(54) MODULAR INBOX SURFACE FOR CONTENT DELIVERY

(71) Applicant: Facebook, Inc., Menlo Park, CA (US)

(72) Inventors: Vinodh Jayaram, Fremont, CA (US); Andrew Yaoshu Song, San Francisco, CA (US); Jonathan David Perlow, San Francisco, CA (US)

(73) Assignee: FACEBOOK, INC., Menlo Park, CA (US)

( * ) Notice: Subject to any disclaimer, the term of this patent is extended or adjusted under 35 U.S.C. 154(b) by 0 days.

(21) Appl. No.: 16/857,516

(22) Filed: Apr. 24, 2020

Related U.S. Application Data

(63) Continuation of application No. 15/273,376, filed on Sep. 21, 2016, now abandoned.

(51) Int. Cl.
| | |
|---|---|
| *G06F 15/16* | (2006.01) |
| *H04L 12/58* | (2006.01) |
| *G06Q 30/02* | (2012.01) |
| *H04W 4/02* | (2018.01) |

(52) U.S. Cl.
CPC ......... *H04L 51/04* (2013.01); *G06Q 30/0239* (2013.01); *G06Q 30/0241* (2013.01); *H04L 51/16* (2013.01); *H04W 4/025* (2013.01)

(58) Field of Classification Search
CPC ..... H04L 51/04; H04L 51/16; G06Q 30/0239; G06Q 30/0241; H04W 4/025
See application file for complete search history.

(56) References Cited

U.S. PATENT DOCUMENTS

| | | | |
|---|---|---|---|
| 8,166,120 B2 * | 4/2012 | Kunz | G06Q 10/107 709/206 |
| 13,271,600 | 9/2012 | Herold et al. | |
| 8,428,777 B1 | 4/2013 | Poursohi et al. | |
| 8,793,591 B1 | 7/2014 | Coleman et al. | |
| 8,886,390 B2 | 11/2014 | Wolfe et al. | |
| 9,311,683 B1 | 4/2016 | Saylor et al. | |
| 9,811,586 B2 | 11/2017 | Wetherell et al. | |
| 9,923,851 B1 | 3/2018 | Sprauve et al. | |
| 10,230,668 B2 | 3/2019 | Ji et al. | |
| 10,412,030 B2 | 9/2019 | McGregor, Jr. et al. | |
| 2002/0120702 A1 | 8/2002 | Schiavone et al. | |
| 2003/0200190 A1 | 10/2003 | Adar et al. | |
| 2007/0061300 A1 * | 3/2007 | Ramer | G06Q 30/0241 |

(Continued)

*Primary Examiner* — Cheikh T Ndiaye
(74) *Attorney, Agent, or Firm* — Kacvinsky Daisak Bluni PLLC

(57) ABSTRACT

Exemplary embodiments relate to improvements in the design of a messaging inbox. The inbox may display different units or "modules" for providing a user with quick access to different inbox functionalities. After a number of recent or unread messages are shown in the inbox's initial interface, the messages end and are replaced with modules. In some embodiments, promotional material may be integrated into a module, or may be integrated as a module. For example, a new message thread may be created to indicate a store in which a discount is offered. The message may appear in a module, or may stand in the place of a module. The promotional material may be selected based on proximity. The messaging service may differentiate between sponsored materials advertising a product or service, and purely beneficial materials such as coupons.

20 Claims, 27 Drawing Sheets

(56) References Cited

U.S. PATENT DOCUMENTS

| | | | |
|---|---|---|---|
| 2007/0157105 A1* | 7/2007 | Owens | G06F 3/04842 715/771 |
| 2008/0162651 A1 | 7/2008 | Madnani | |
| 2008/0189367 A1 | 8/2008 | Okumura | |
| 2008/0220877 A1 | 9/2008 | Guthrie | |
| 2011/0179164 A1 | 7/2011 | Memon et al. | |
| 2012/0102126 A1 | 4/2012 | Murphy et al. | |
| 2012/0246337 A1 | 9/2012 | Ross | |
| 2012/0278388 A1 | 11/2012 | Kleinbart et al. | |
| 2012/0322041 A1 | 12/2012 | Weisman | |
| 2014/0172840 A1 | 6/2014 | Kumar et al. | |
| 2014/0241216 A1 | 8/2014 | Cheng et al. | |
| 2014/0324627 A1* | 10/2014 | Haver | G06Q 30/0273 705/26.9 |
| 2015/0040027 A1 | 2/2015 | Cheng et al. | |
| 2015/0172462 A1 | 6/2015 | Cudak et al. | |
| 2015/0188869 A1* | 7/2015 | Gilad | H04L 51/22 715/752 |
| 2015/0317666 A1* | 11/2015 | Pygnasak | G06Q 30/0226 705/14.27 |
| 2016/0034977 A1* | 2/2016 | Bhaowal | H04L 51/063 707/722 |
| 2016/0119390 A1 | 4/2016 | Moeinifar | |
| 2016/0191450 A1* | 6/2016 | Lineberger | G06Q 30/0241 709/206 |
| 2016/0283978 A1* | 9/2016 | Rabbat | G06F 3/0481 |
| 2016/0359957 A1* | 12/2016 | Laliberte | G06Q 30/0481 |
| 2017/0034085 A1* | 2/2017 | Bijor | H04L 51/16 |
| 2017/0093779 A1 | 3/2017 | Taliaferro et al. | |
| 2017/0250935 A1 | 8/2017 | Rosenberg | |
| 2017/0250936 A1 | 8/2017 | Rosenberg et al. | |
| 2018/0060432 A1 | 3/2018 | Kenthapadi et al. | |
| 2018/0107685 A1 | 4/2018 | Kale et al. | |
| 2018/0108066 A1 | 4/2018 | Kale et al. | |
| 2018/0150524 A1 | 5/2018 | Anger et al. | |
| 2019/0347326 A1 | 11/2019 | Kozhaya et al. | |
| 2020/0050942 A1 | 2/2020 | Sun et al. | |
| 2020/0065697 A1 | 2/2020 | Watson et al. | |
| 2020/0082928 A1 | 3/2020 | Wu et al. | |
| 2020/0137002 A1 | 4/2020 | Chavda | |

\* cited by examiner

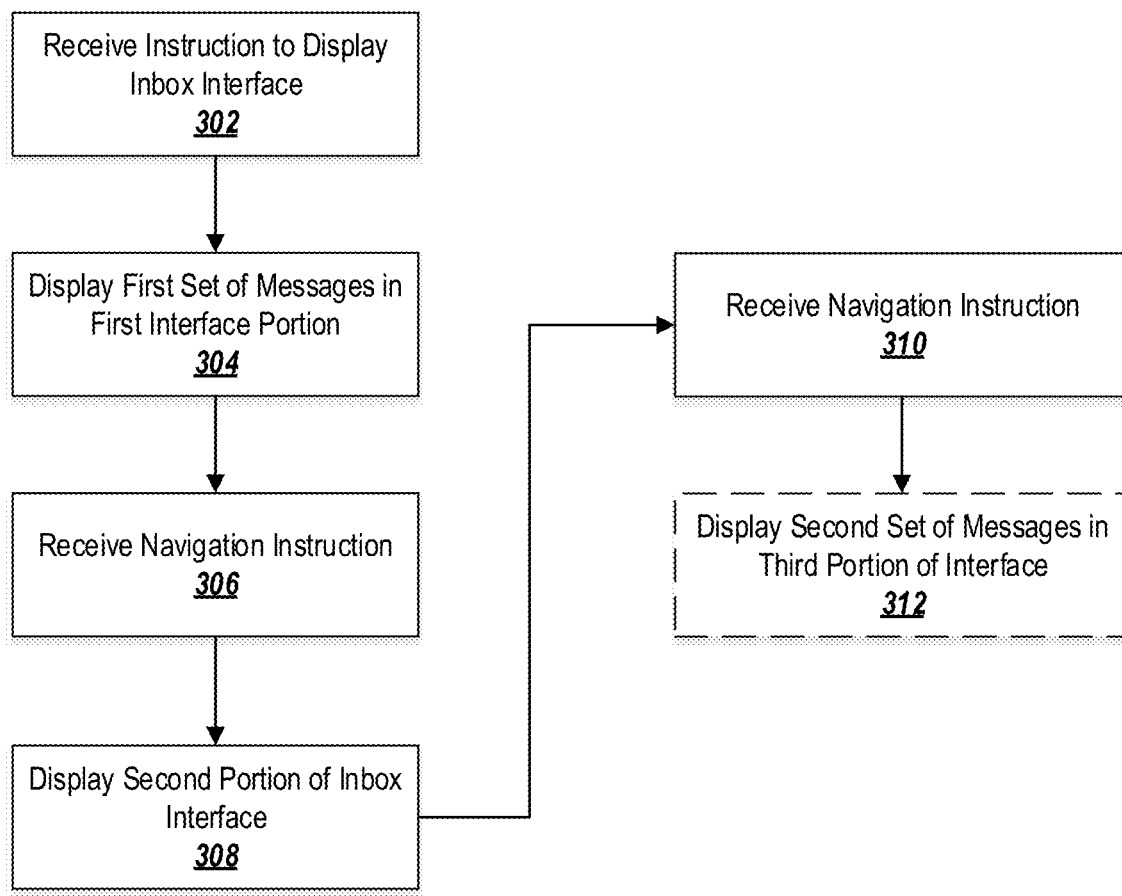

Sharing Module Logic
*438*

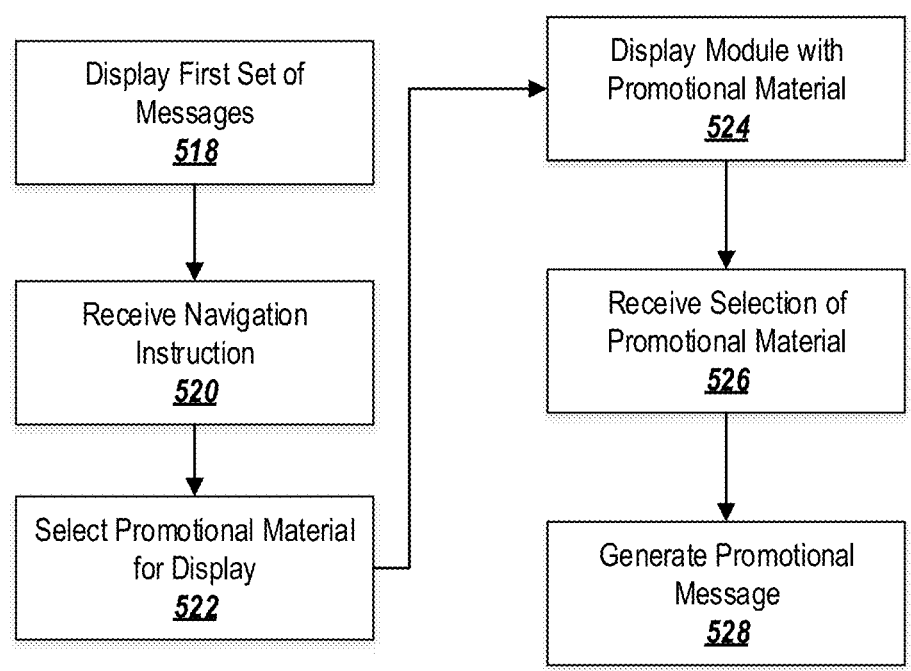

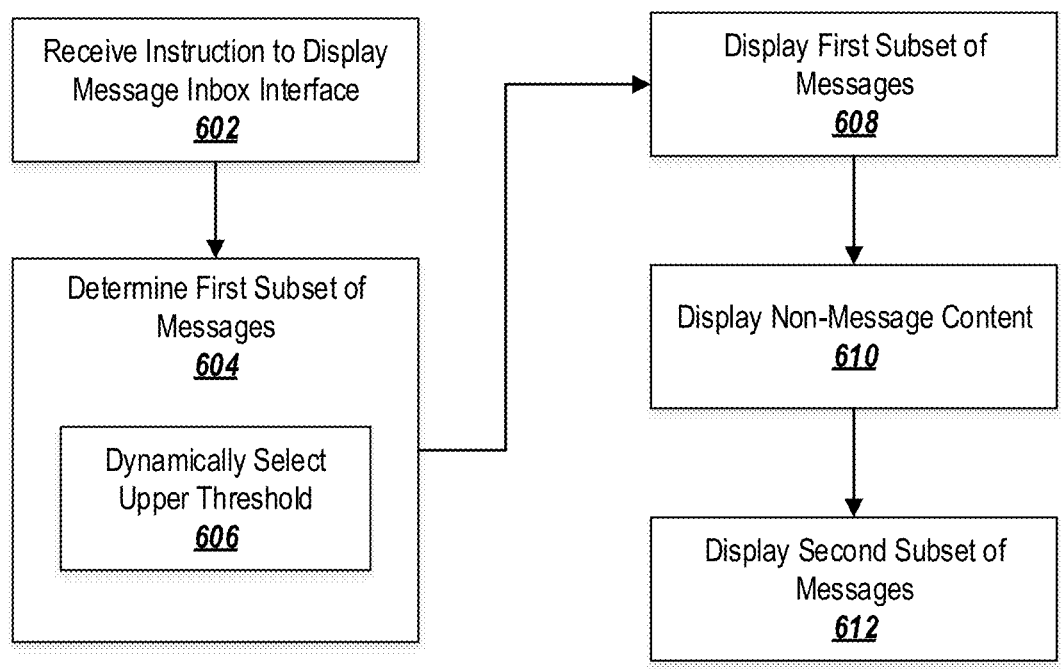

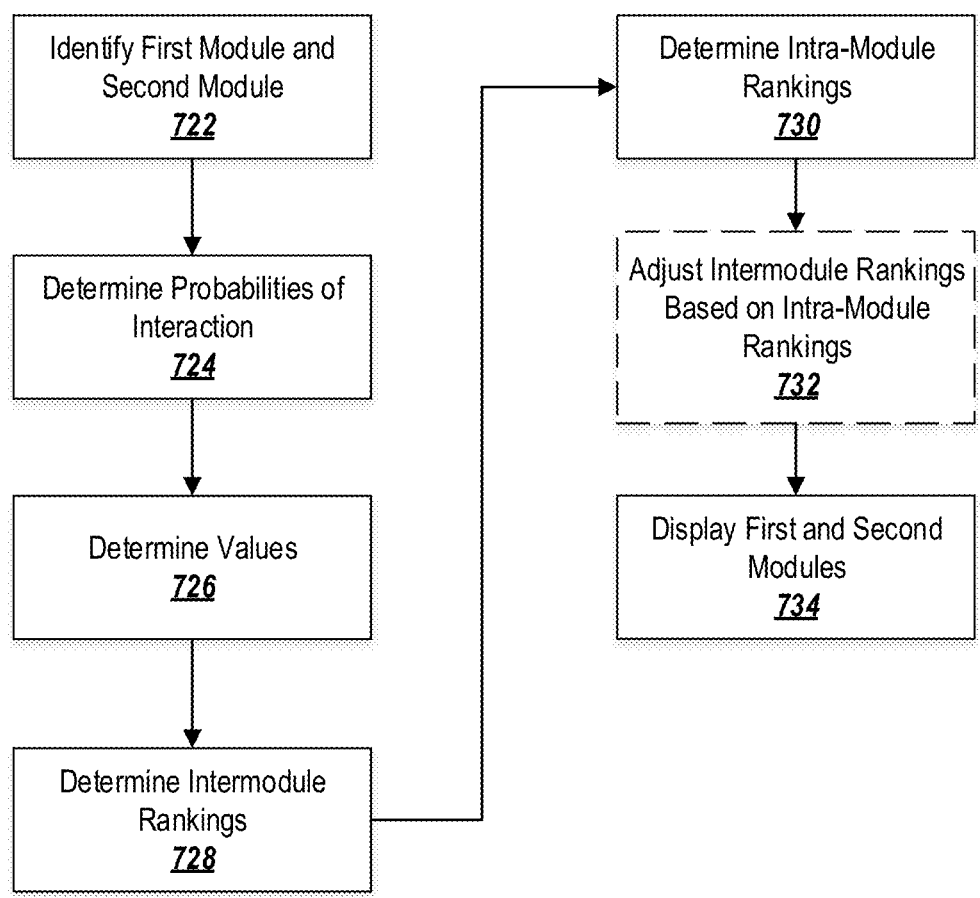

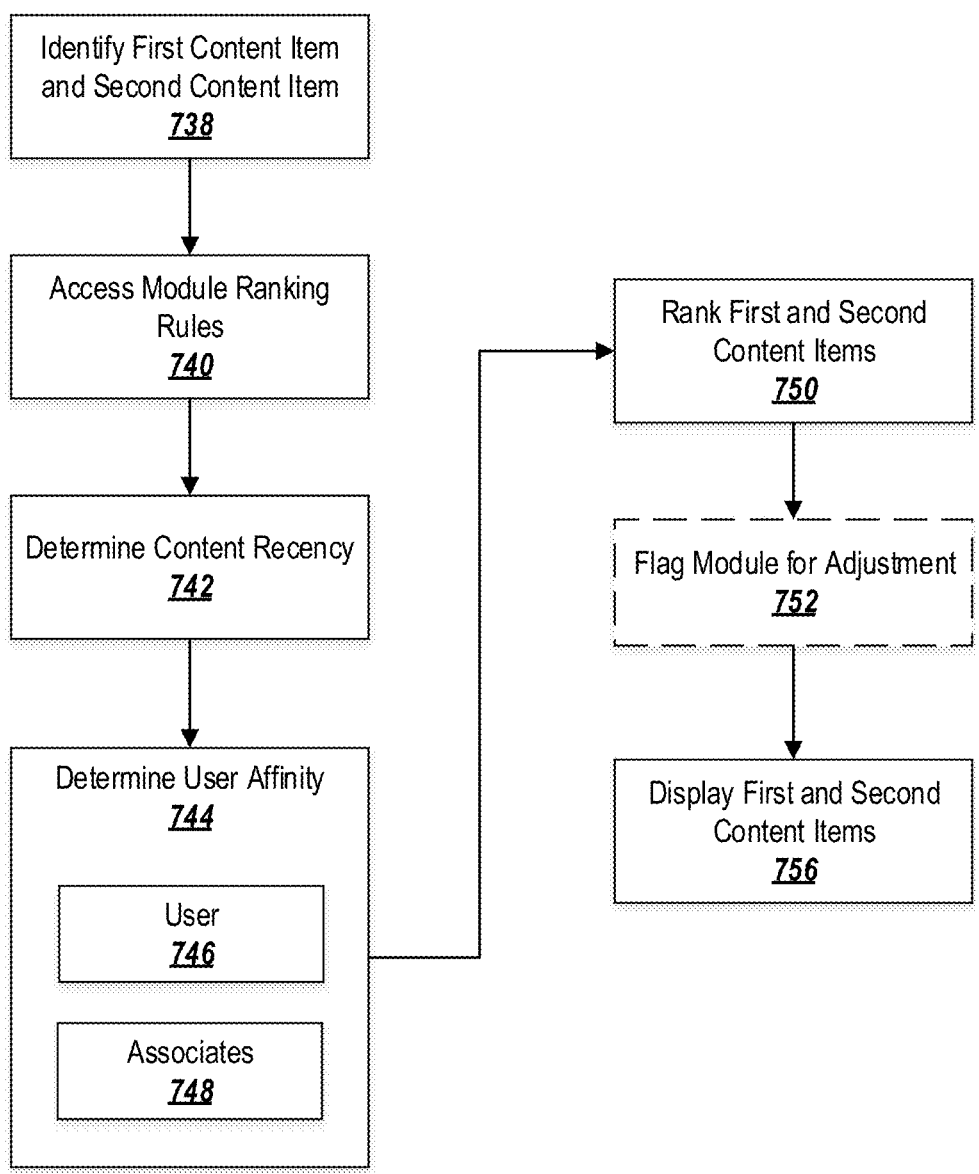

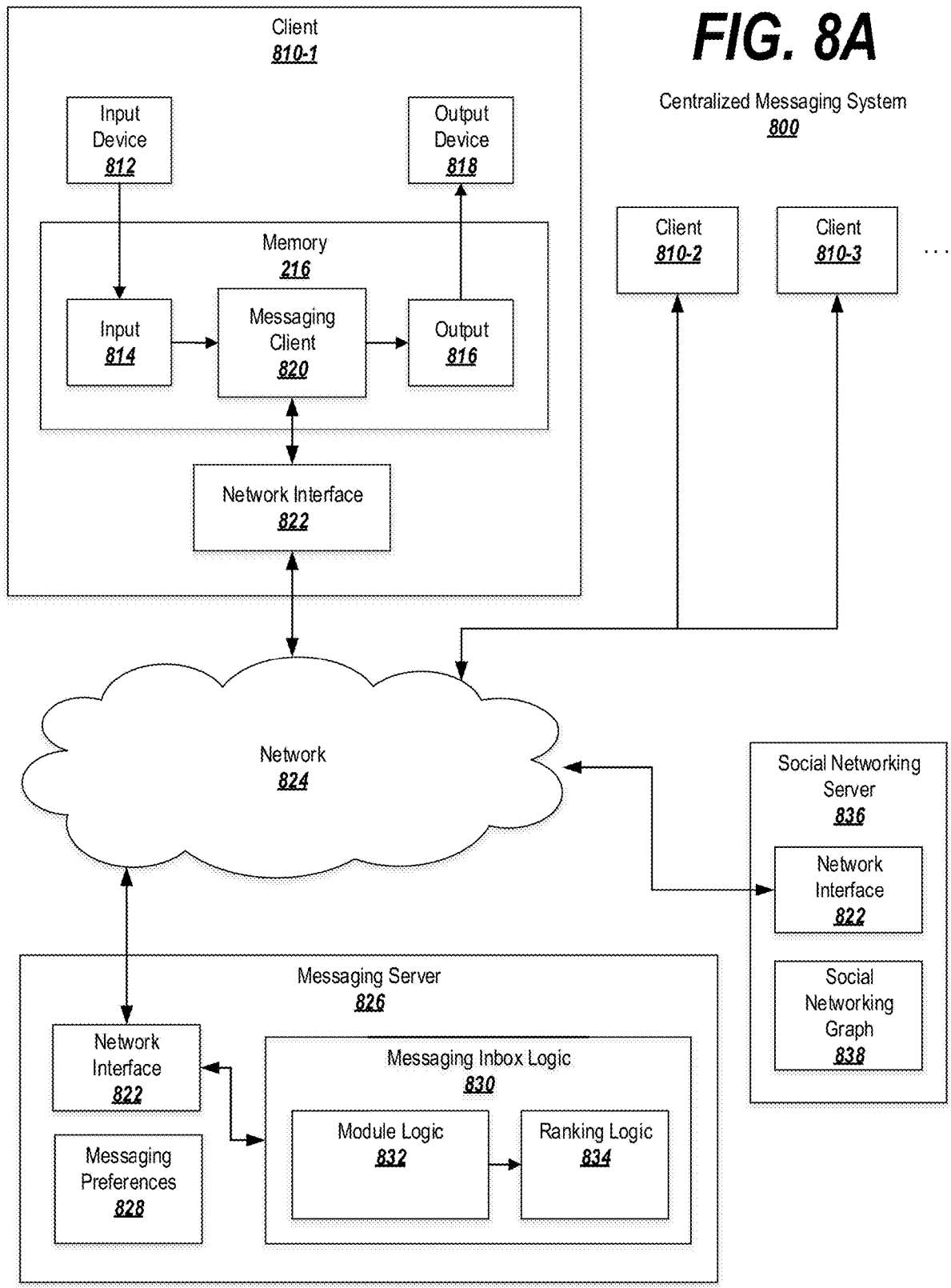

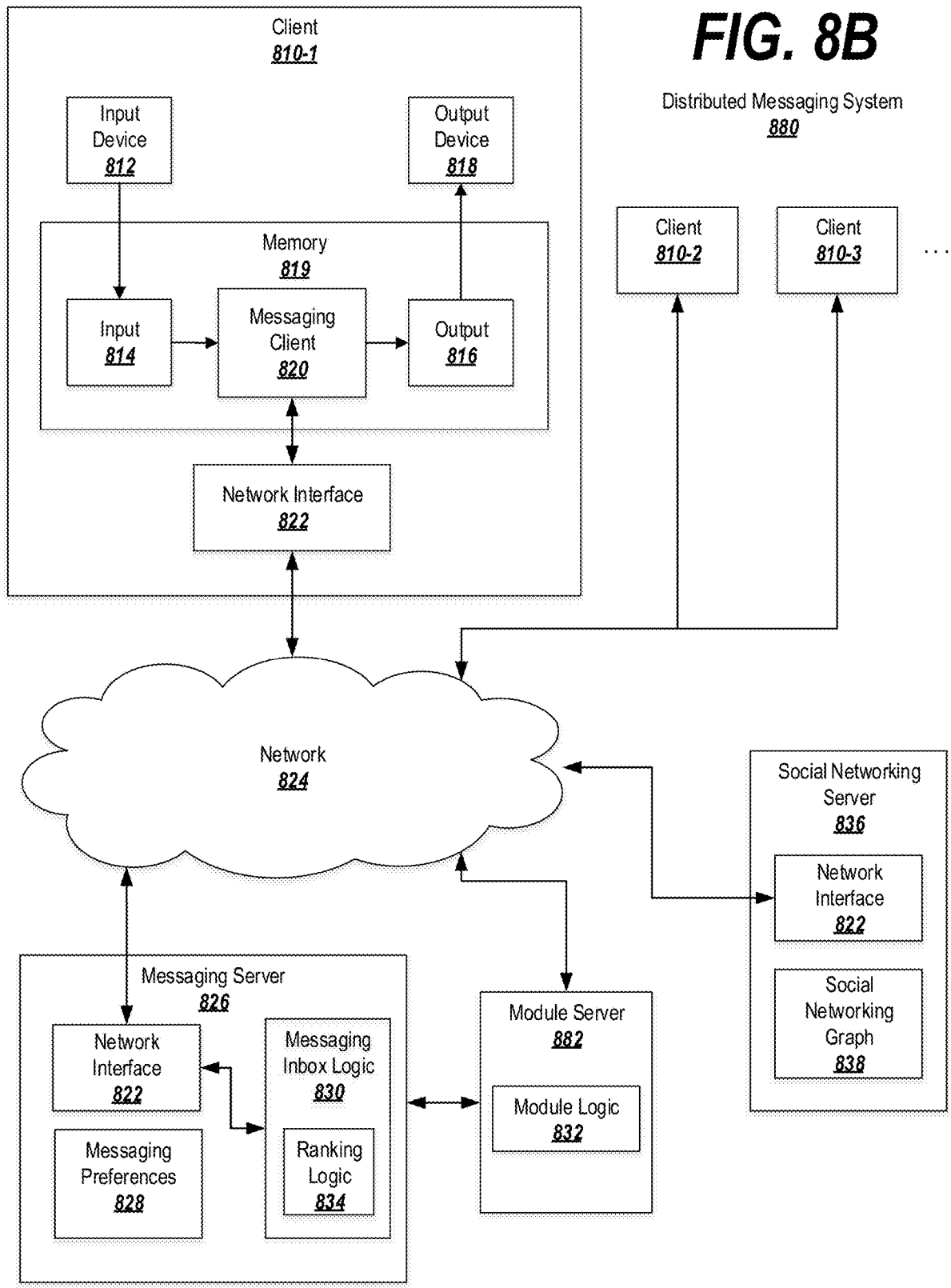

MODULAR INBOX SURFACE FOR CONTENT DELIVERY

RELATED APPLICATIONS

This application claims the benefit of priority under 35 U.S.C. § 119(e) to U.S. patent application Ser. No. 15/272,376, titled "Modular Inbox Surface for Content Delivery," filed on Sep. 21, 2016, which is hereby incorporated by reference in its entirety.

BACKGROUND

Messaging systems, such as instant messaging systems and short message service ("SMS") systems, allow users to communicate with each other by exchanging messages. Messaging services may also provide capabilities beyond exchanging messages, but in many cases the user may not be aware of the additional capabilities or how to use them. In some situations, the additional capabilities may be relatively difficult to locate in a messaging application, or their use may be non-intuitive. As a result, these additional capabilities may be underutilized. Moreover, users of the messaging service who might be relatively active users if they were aware of the additional capabilities may instead become less active.

BRIEF DESCRIPTION OF THE DRAWINGS

FIG. 3 is a flowchart depicting an exemplary process for displaying an inbox interface including one or more modules;

FIG. 5D is a flowchart depicting an exemplary process for providing promotional content in a module;

FIG. 6 is a flowchart depicting an exemplary process for determining a transition point between a first group of messages and a set of one or more modules;

FIG. 7B is a flowchart depicting an exemplary process for determining an inter-module rank;

FIG. 7C is a flowchart depicting an exemplary process for determining an intra-module rank;

FIG. 8A is a block diagram providing an overview of a system including an exemplary centralized messaging service;

FIG. 8B is a block diagram providing an overview of a system including an exemplary distributed messaging service;

DETAILED DESCRIPTION

Figure 1A:
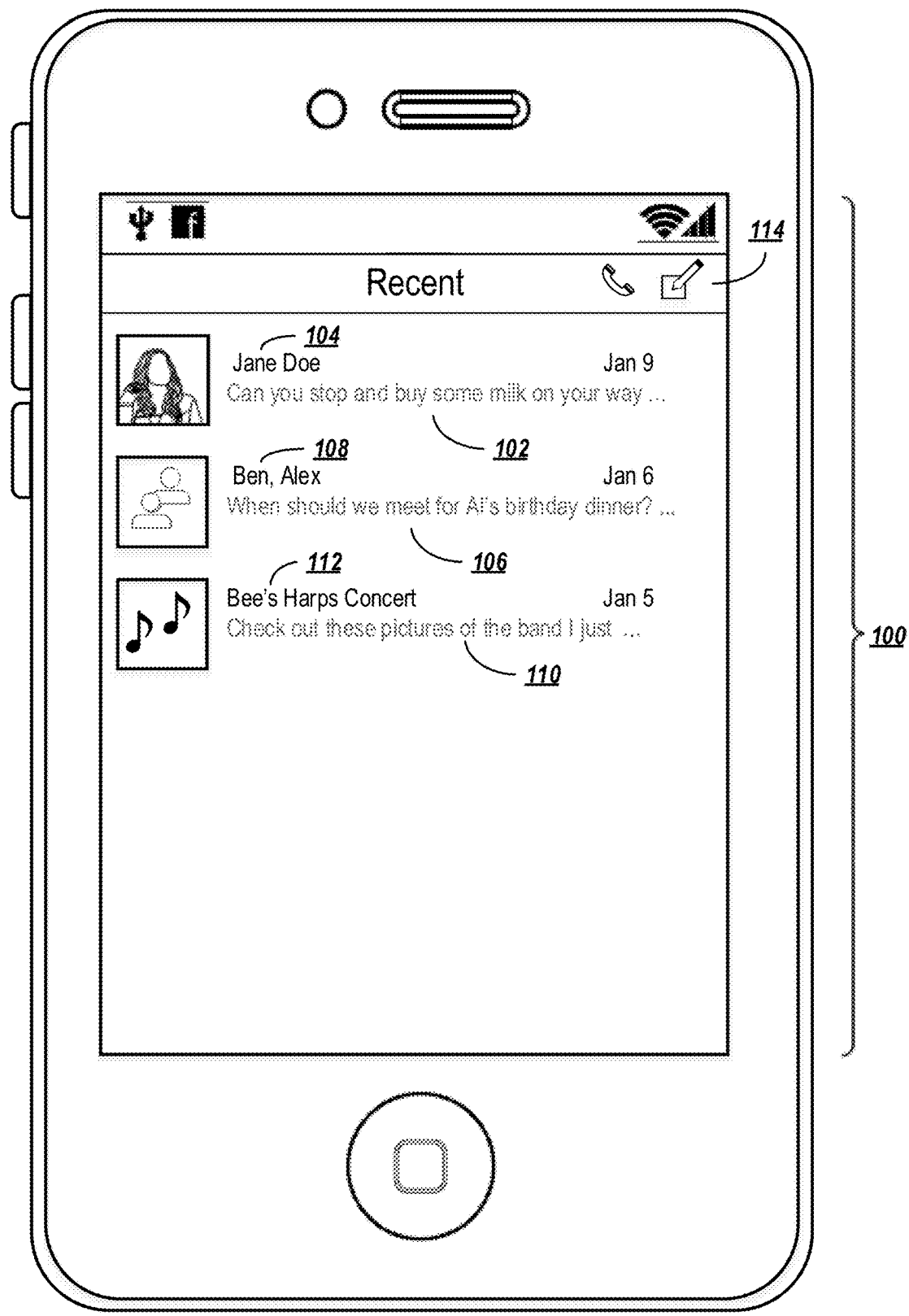
FIG. 1A depicts an exemplary messaging interface including several types of individual and group messages.

Messaging applications may provide an inbox that allows a user to read and send messages. However, a messaging application may provide additional functionality beyond reading and sending messages, such as playing games, sending money to a friend, viewing which other users are online to spur a conversation, etc. If these additional functions are hidden in menus or accessed through special commands or gestures, many users will rarely or never use them. The users may not know that this functionality exists or accessing the functionality may prove too cumbersome to encourage regular use. Because this functionality can spur increased use of the messaging application, administrators of the messaging service may wish to encourage its use.

In a messaging inbox displaying messages, it is often the case that some messages are more important or valuable to a user than others. For example, it may be highly likely that a user will wish to access recent messages and unread messages, whereas relatively stale messages or messages that have been previously read are less likely to be accessed.

According to exemplary embodiments, these insights are combined to provide a modular inbox that encourages use of the messaging service's full functionality, while also providing ready access to the user's most important or valuable messages. In the modular inbox, the inbox may be divided into different inbox units or modules. The modules may provide a user with quick and convenient access to different inbox functionalities that the user might not otherwise be aware of (or inclined to use on a regular basis).

After a number of messages are shown in the inbox's initial display, the messages end and are replaced with modules. The number of messages to display before switching to modules (referred to herein as a messaging cliff) is determined based on a minimum threshold and a dynamic maximum threshold that can differ from user-to-user and based on the context (e.g., the time of day).

The point where the inbox transitions from the recent messages to the modules (the messaging cliff) may be determined statically or dynamically. A static determination may involve transitioning to the modules after a predetermined number of recent messages. A dynamic determination may be made based on, for example, selecting a number of messages to display that falls within a minimum number of messages and a maximum number of messages. The minimum may be, for example, 4-8 messages and may be based on a predetermined minimum message threshold. The maximum number of messages may be dynamic, and may be based on the current time of day, the number of message threads in which the user is participating in an active conversation, or the number of unread messages in the user's inbox (e.g., the cliff may be set to display all unread messages within a certain time frame, which may include gaps where read messages have been filtered out). The maximum number of messages displayed may be different for different users. For example, a power user may receive a large number of messages over a short time frame. Such a user might see messages only from the very recent past but might have a higher threshold for the number of messages to display. An infrequent user, on the other hand, might see fewer messages over a longer time frame. User activity may be determined based on historical usage of the messaging application or messaging service.

The modules section of the inbox differs from the message display section of the inbox in that the modules are primarily configured for functionality other than the displaying of messages or message threads. Modules may provide different kinds of functionality, such as showing active users, suggesting new activities, or making it easy to share content from a device (e.g., through the device's camera roll or photo album), a social networking service, or another source. The modules may include modules for sharable articles/videos/pictures that allow a user to select content to be provided to other messaging service users. Modules can also include, or can be, advertisements.

Further embodiments provide modules relating to the sharing of content from a social networking service associated with the messaging service. For example, some modules may allow a user to share articles, videos, or pictures from the social networking service. Exemplary interfaces simplify the sharing procedure by providing content recommendations, which may be retrieved from the social networking service based on consumption information. Alternatively or in addition, the content may be retrieved from a location outside the social networking service, or from multiple sites.

Content items within modules can be ranked to determine which intra-module order to display the content items. The content may be ranked based on a number of metrics, such as recency of access, interaction time, and/or an enjoyment metric personalized to a given user. The intra-module content ranking scheme may be defined on a module-by-module basis. Content may be displayed in the sharing module based on the rank.

In addition to (or alternatively from) ranking the content within a module, the modules may also be ranked against each other in order to determine which order to show the modules. Inter-module ranking may be determined based on ranking metrics, such as the user's estimated interest in the module, the estimated interest in the module among a user base of the messaging service, and a value of displaying the module to the messaging service or an associate of the messaging service. Inter-module ranking may be determined at a server communicating with a client device, although the inter-module ranking scheme may also be extensible with offline models.

The intra-module content ranking may be used to affect the inter-module ranking. For example, if a particular content item in a low-ranked module is determined to be particularly pertinent or exciting (e.g., an article is currently being viewed by a large number of people on a social network), then this may cause the content item's module to be elevated in the inter-module ranking. In some circumstances, the module may even be elevated above the messages displayed in the first section of the inbox.

When sharing content, the module may suggest a group of recommended recipients. The group may include members selected based on the content (e.g., who is considered the most likely to enjoy the content) and/or metrics based on users with whom the sharing user has historically shared similar content.

When sharing local or social networking media, exemplary embodiments provide simple low-friction ways to share the material. In general, the system may provide an interface displaying content recommendations and a list of suggested users with whom the content may be shared. Upon selecting the content and a list of target users, the original user may simply press send, and the messaging service will automatically generate suitable messages and/or message threads to share the content.

Still further, some modules may be used to deliver promotional materials. Promotional material may be in the form of promotional content items, such as individual offers or advertisements. The promotional content items may be presented in a dedicated module (e.g., a promotional materials module), and/or may be integrated into other modules (e.g., providing a promotional content item among the shareable articles in an articles module). In some embodiments, a business may purchase a higher ranking for their promotional content item to allow the promotional content item to be displayed earlier in the list of modules or within a given module.

Interacting with the promotional content items may cause a new message or thread to be delivered to the user's inbox. Such a message may include a code that offers a discount when scanned in a retail location. The messages and/or promotional content items may be generated based on proximity. In one example, promotional content items may be displayed based on a user's affinity, and interacting with a promotional content item may allow a user to claim an offer from a provider. When the user's device is identified at a location proximate to a retail location for the provider, the user may be sent a message prompting the user to enter the retail location and scan the code to receive a discount.

In some embodiments, sponsored promotional content items (e.g., advertisements) may be distinguished from discount offers, which are generally perceived to be purely beneficial and thus may be better tolerated by users in certain circumstances. Different types of promotional content items may be prompted in different ways, and interacting with different types of promotional content items may produce different results. For example, purely sponsored promotional content items may be displayed in an advertising-specific module, whereas discount items may be presented among other content items in a different module. In some cases, purely sponsored promotional content items may be displayed among other content items (e.g., when the user is determined to be in a location proximate to a provider of the promotional content item). In another example, interacting with a discount offer may cause an interface to be presented allowing the user to share the discount offer with their friends (e.g., to encourage the friends to go to a coffee shop together), whereas interacting with a promotional content item containing an advertisement might open a message thread with the sponsor of the promotional content item.

After scrolling through the recent messages and reaching the cliff, the user may scroll through the modules. When the available modules are exhausted (or after displaying a predetermined or dynamically determined number of modules), the inbox may transition back to older unread messages. Alternatively or in addition, older or unread threads may be collapsed into the top section, before the cliff.

As an aid to understanding, a series of examples will first be presented before detailed descriptions of the underlying implementations are described. It is noted that these examples are intended to be illustrative only and that the present invention is not limited to the embodiments shown.

Reference is now made to the drawings, wherein like reference numerals are used to refer to like elements throughout. In the following description, for purposes of explanation, numerous specific details are set forth in order to provide a thorough understanding thereof. However, the novel embodiments can be practiced without these specific details. In other instances, well known structures and devices are shown in block diagram form in order to facilitate a description thereof. The intention is to cover all modifications, equivalents, and alternatives consistent with the claimed subject matter.

In the Figures and the accompanying description, the designations "a" and "b" and "c" (and similar designators) are intended to be variables representing any positive integer. Thus, for example, if an implementation sets a value for a=5, then a complete set of components 122 illustrated as components 122-1 through 122-a may include components 122-1, 122-2, 122-3, 122-4, and 122-5. The embodiments are not limited in this context.

Messaging Overview

A general overview of messaging techniques is now described.

Users may interact with a messaging system through a client application. FIG. 1A depicts an example of a client application displaying a messaging interface 100. The messaging interface 100 of FIG. 1A shows an exemplary summary screen that provides an overview of messages recently sent to (or by) the user of the client application.

Messaging systems may support a variety of different types of messages. For example, the messaging interface 100 includes a summary of a one-to-one (or individual) message 102. A one-to-one message is a message exchanged between two entities, so that only the two entities can see and participate in the conversation. For example, in the one-to-one message 102, the current user (Jack Doe) recently received a message from his wife, Jane Doe. The other participant in the conversation is indicated in the interface 100 using an identifier 104 (including a name and profile picture, in this example). Only Jack and Jane participate in the conversation, and only Jack and Jane can view the conversation.

Another message type supported by the messaging system is a group conversation. In a group conversation, multiple users see and participate in the conversation. FIG. 1A depicts an exemplary summary of a group conversation 106. In the summary of the group conversation 106, each of the other users participating in the conversation is indicated by respective identifiers 108. In this case, the identifiers include the names or handles of the other users participating in the group conversation, and an icon to indicate that the conversation is a group conversation. For example, in this case the current user (Jack) is participating in a conversation with his friends Ben and Alex. Jack, Ben, and Alex can each see all of the messages in the conversation (regardless of who sent the message) and can send messages to the group.

Another type of message supported by the messaging system is a message between one or more users and an organization (such as a business) or event. For example, FIG. 1A shows an event message 110 sent by the current user (Jack) to the page of an event being organized through a social network. The identifier 112 identifies the name of the event, and an icon is presented identifying this particular event is a concert. In an event message 110, all participants in the event (as a participant is defined, e.g., by the event's social networking page) can view and send event messages 110. Participants may include, for example, people attending the event, fans of the event that have signed up with the event's page to receive messages about the event, event organizers, etc.

By selecting an existing message summary 102, 106, 110, the user can view messages in an existing conversation and add new messages to the conversation. Moreover, the interface 100 includes interface elements 114 allowing the user to create a new message.

Figure 1B:
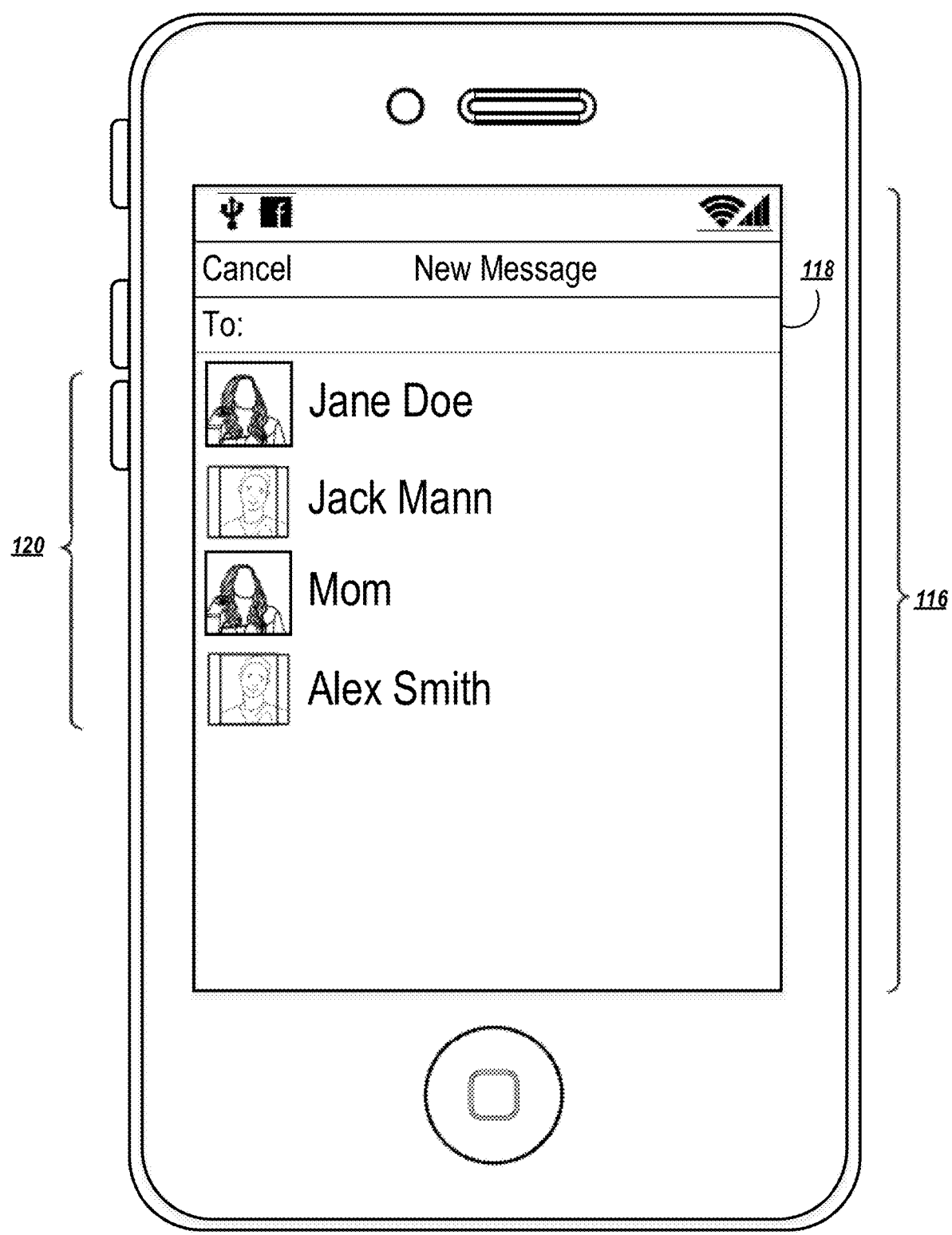
FIG. 1B depicts an exemplary message composition interface.

For example, FIG. 1B depicts an interface 116 displayed by the messaging client application in response to receiving a selection of the "compose" interface element 114. A "new message" window is displayed in the interface 116. The new message window includes a recipient field 118 for allowing the user to manually enter identifiers for one or more recipients. If available, the user's contacts list 120 may also be displayed in the interface 116 in order to simplify the selection of the recipients.

Figure 1C:
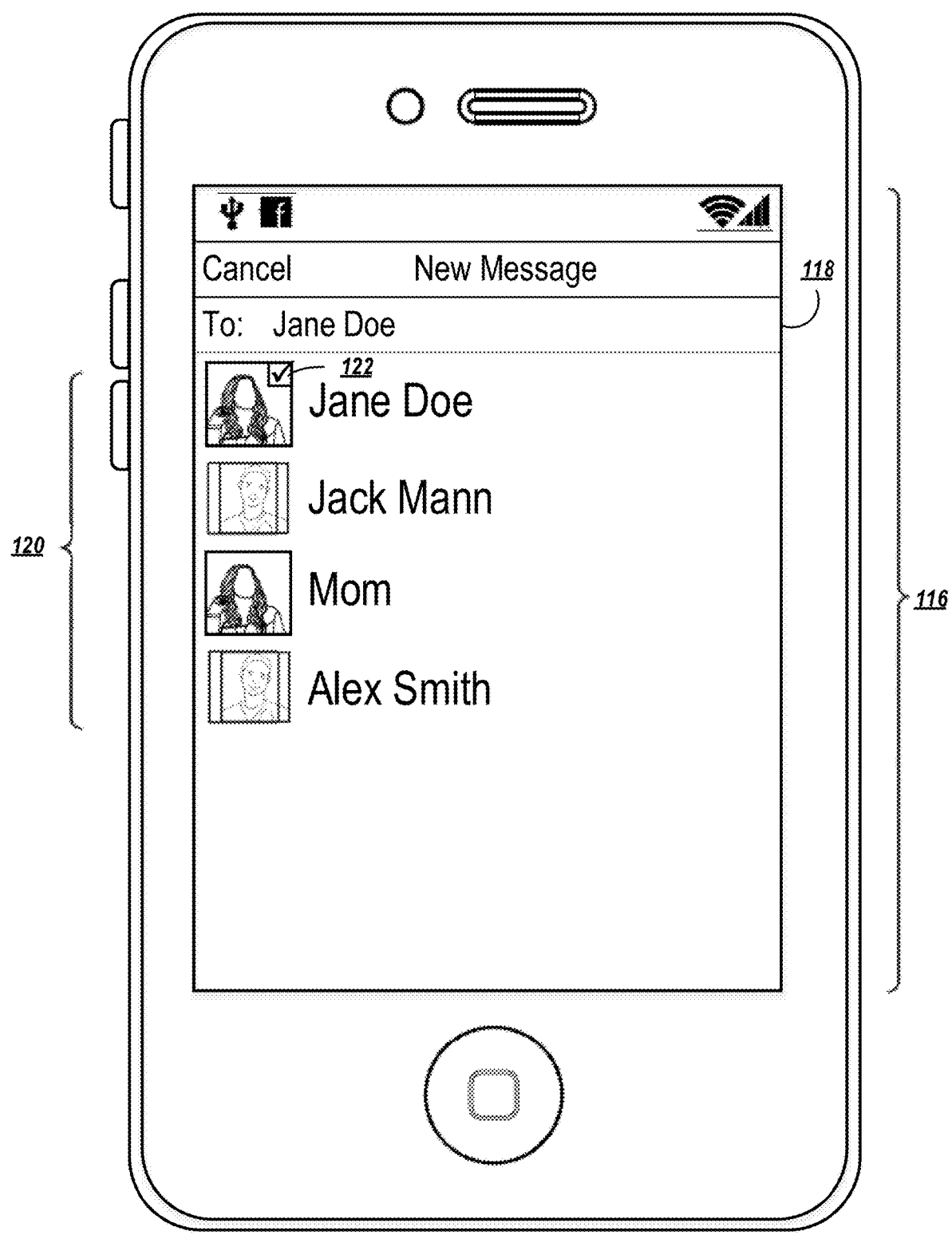
FIG. 1C depicts an example of selecting a recipient of a message in a messaging interface.

In the example of FIG. 1C, the user has entered the identifier of a recipient in the recipient field 118. In order to indicate the recipient's inclusion in the recipients list, a selection indication 122 is displayed on the recipient's icon in the contacts list 120.

Figure 1D:
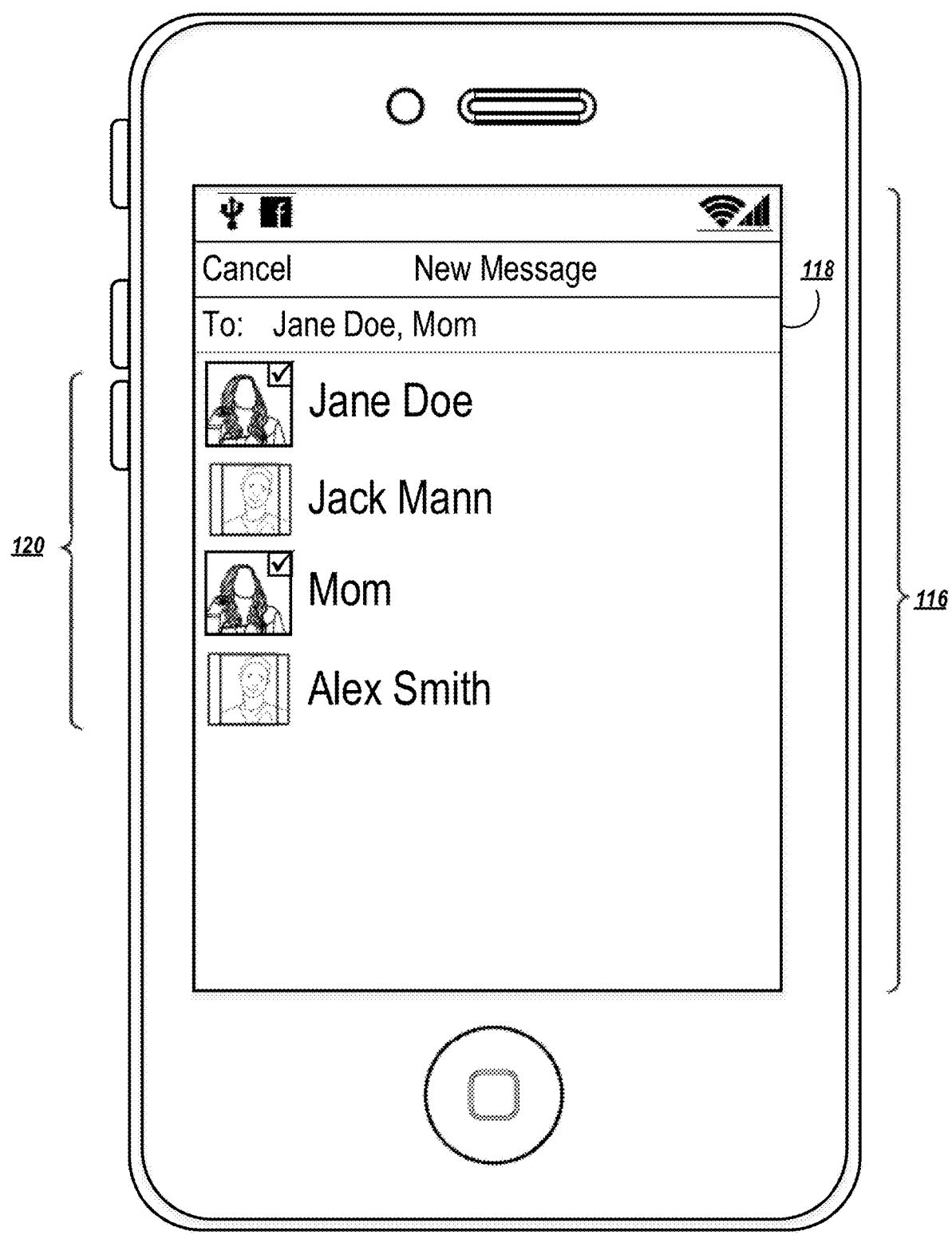
FIG. 1D depicts an example of selecting a group of recipients of a message in a messaging interface.

It is possible to select more than recipient in the interface 116 in order to create a group message, e.g. by manually adding multiple recipients in the recipient filed 118, selecting multiple contacts in the contacts list 120, or a combination of methods. FIG. 1D depicts an example of such a group selection.

This brief summary is intended to serve as a non-limiting introduction to the concepts discussed in more detail below, in connection with FIGS. 2-8. However, before discussing further exemplary embodiments, a brief note on data privacy is first provided. A more detailed description of privacy settings and authentication will be addressed in connection with the following Figures.

A Note on Data Privacy

Some embodiments described herein make use of training data or metrics that may include information voluntarily provided by one or more users. In such embodiments, data privacy may be protected in a number of ways.

For example, the user may be required to opt in to any data collection before user data is collected or used. The user may also be provided with the opportunity to opt out of any data collection. Before opting in to data collection, the user may be provided with a description of the ways in which the data will be used, how long the data will be retained, and the safeguards that are in place to protect the data from disclosure.

Any information identifying the user from which the data was collected may be purged or disassociated from the data. In the event that any identifying information needs to be retained (e.g., to meet regulatory requirements), the user may be informed of the collection of the identifying information, the uses that will be made of the identifying information, and the amount of time that the identifying information will be retained. Information specifically identifying the user may be removed and may be replaced with, for example, a generic identification number or other non-specific form of identification.

Once collected, the data may be stored in a secure data storage location that includes safeguards to prevent unauthorized access to the data. The data may be stored in an encrypted format. Identifying information and/or non-identifying information may be purged from the data storage after a predetermined period of time.

Although particular privacy protection techniques are described herein for purposes of illustration, one of ordinary skill in the art will recognize that privacy protected in other manners as well. Further details regarding data privacy are discussed below in the section describing network embodiments.

Figure 2A:
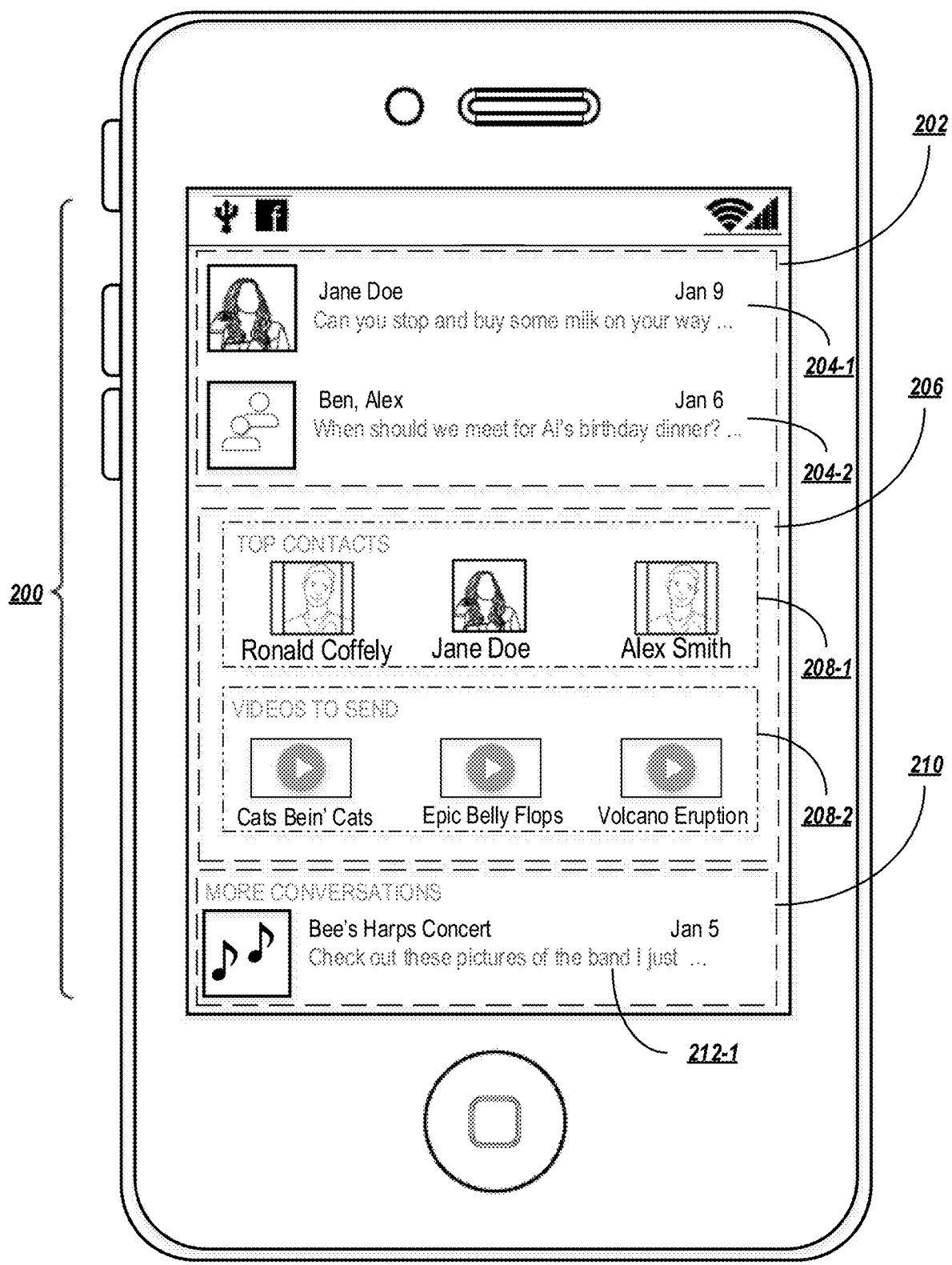
FIG. 2A depicts an exemplary interface for a messaging inbox including a first portion displaying a first set of messages, a second portion displaying one or more modules, and a third portion displaying a second set of messages.

Assuming a user's privacy conditions are met, exemplary embodiments may be deployed in a wide variety of messaging systems, including messaging in a social network or on a mobile device (e.g., through a messaging client application or via short message service), among other possibilities. An overview of a messaging system is now provided Modular Inbox Overview FIG. 2A depicts an exemplary interface 200 for a messaging inbox. The interface includes a first portion 202 for displaying a first set of messages 204, a second portion 206 displaying one or more modules 208, and a third portion 210 displaying a second set of messages 212.

Although FIG. 2A depicts each of the first portion 202, the second portion 206, and the third portion 208 together on a single screen of the device, any or all of the interface portions may extend to or beyond a single device screen. The user may navigate through the interface 200, for example by scrolling.

The first set of messages 204 may be the most relevant or recent messages, whereas the second set of messages 212 may be less relevant or recent messages. The transition point between the first set of messages 204 and the second set of messages 212 is referred to herein as a message cliff. Techniques for determining which messages to include in the first set of messages 204, and which to include in the second set of messages 212, are covered in detail in the section below addressing The Cliff.

Scrolling through the interface 200 may cause the interface 200 to expose or display the first portion 202, the second portion 206, and the third portion 210, respectively. For example, the display may first render the first portion 202 of the interface 200. If the messages 204 of the first portion 202 do not occupy all of the display space available to the interface 200, then at least a part of the second portion 206 may also be displayed (as much as will fit in the space left over after the first portion 202 is displayed). If the messages 204 of the first portion 202 occupy more space than is immediately available to the interface 200, then scrolling through the interface 200 may cause additional messages in the first set of messages 204 to be displayed, until the user reaches the messaging cliff. If the user continues to scroll after reaching the messaging cliff, then the second portion 206 including the modules 208 may be displayed. The user may continue to scroll through the modules 208 until the available modules are exhausted. At this point, the interface 200 may begin to display the third portion 210 including the second set of messages 212.

In the example of FIG. 2A, the messaging inbox displays messages up to a certain point (the first set of messages 204), then modules 208, and then the second set of the user's messages 212 (in the third portion 210 of the interface 200). As an alternative, or in addition to, this approach, some or all of the second set of messages 212 (messages falling after the messaging cliff) may be collapsed into the first portion 202 of the interface 200.

Figure 2B:
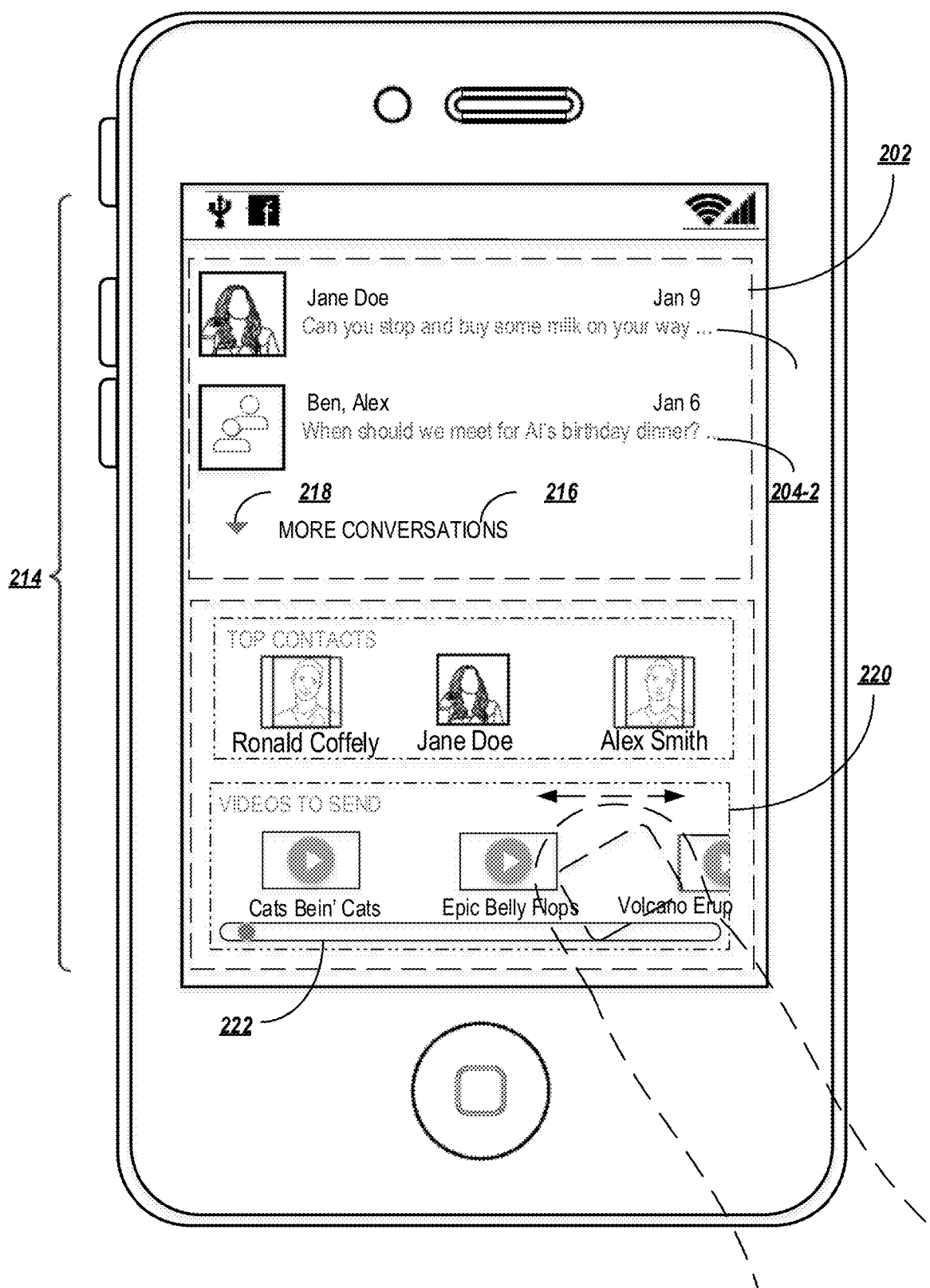
FIG. 2B depicts an exemplary interface for a messaging inbox in which a second set of messages is displayed in the first portion of the interface including the first set of messages.

For example, FIG. 2B depicts an exemplary interface 214 for a messaging inbox in which a second set of messages is displayable in the first portion 202 of the interface 200, which also includes the first set of messages 204. In the interface 214, the second set of messages may be initially hidden behind a collapsible heading 216 having an expandable interface element 218. Interacting with the expandable interface element 218 may cause the second set of messages 204 to be displayed.

As further depicted in FIG. 2B, in addition to scrolling through the interface 200 as a whole, individual modules 208 may also be scrollable. The modules 208 may present a predetermined amount of content or options. For example, a videos module 220 may display a number of videos from a social networking service that the system considers the current user to be most likely to share with friends. If the system determines that the amount of content can fit on the display of the user's device (e.g., based on the screen width and resolution available to the interface 200), then the content may be entirely displayed within the width of the interface, in a section reserved for the module 208.

On the other hand, if the amount of content does not entirely fit on the display (or if the module 208 allows for a potentially unlimited or amount of content), then the system may provide options for allowing the user to scroll through the videos module 220. The system may present an option to scroll horizontally through the content (e.g., by allowing a user to gesture on a touch display with a left- or right-swipe), vertically through the content (e.g., by allowing a user to gesture on the touch display with an up- or down-swipe within an area reserved for the module), or both. In the depicted example, a horizontal scroll bar 222 shows the user's progress through the available content.

Exemplary Modules

The second portion 206 of the interface 200 may include multiple different sections providing different types of modules 208. Exemplary modules 208 are discussed below, although it is contemplated that additional types of modules may also be used. Exemplary embodiments may display some or all of the different types of modules 208 in the second portion 206 of the interface 200. The modules 208 to be displayed may be selected based on the user's sharing history or interactions with a social networking service; those modules that the social networking service considers are most likely to be useful to the user may be selected for display.

Figure 2C:
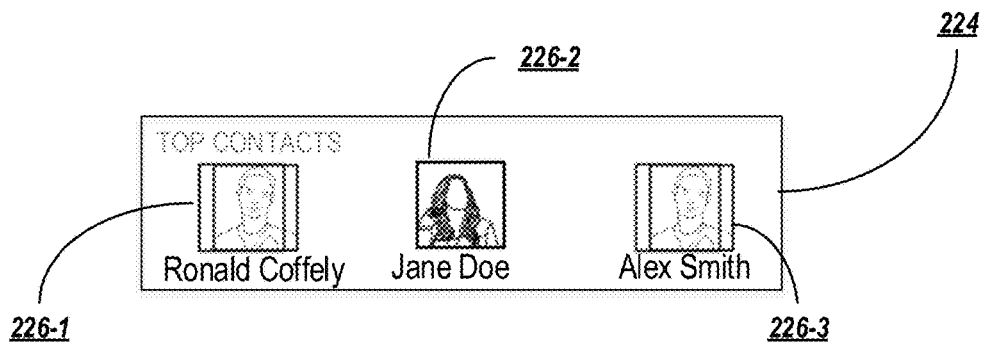
FIG. 2C depicts an example of a top contacts module.

FIG. 2C depicts an example of a top contacts module 224. The top contacts module 224 may include a list of top contacts 226 from the messaging inbox owner's contacts list. The top contacts 226 may be selected from the contacts list based on, for example, the inbox owner's messaging history (e.g., which users the inbox owner has messaged most frequently, most recently, at certain times of the day, etc.), and/or other metrics such as an affinity of the inbox owner for the contact, a proximity of the contact to the inbox owner, or context-sensitive information such as a current or future change in location.

For example, if an out-of-town contact is traveling to the inbox owner's location, then the out-of-town contact may be displayed in the top contacts module 224, even if they would not otherwise be included based on other metrics. In another embodiment, the contacts may be selected based on properties of the contact (such as whether it is the contact's birthday). In yet another example, the system may add contacts to the list if the contact has not been messaged by the inbox owner for more than a predetermined period of time, particularly if the contact was someone that the message owner previously contacted often (e.g., to encourage the inbox owner to message the contact). Explanatory information (e.g., "User X will be visiting City Y from Date A to Date B") may be displayed in the top contacts module 224.

A predetermined number of top contacts 226 may be selected for display in the top contacts module 220. Optionally, the predetermined number may be user-configurable so that the user may specify how many top contacts to display. If the number of contacts displayed in the top contacts module 224 is too great to fit within the space reserved for the top contacts module 224 on the display, then the top contacts module 224 may be scrollable (e.g., with a horizontal scroll).

Figure 2D:
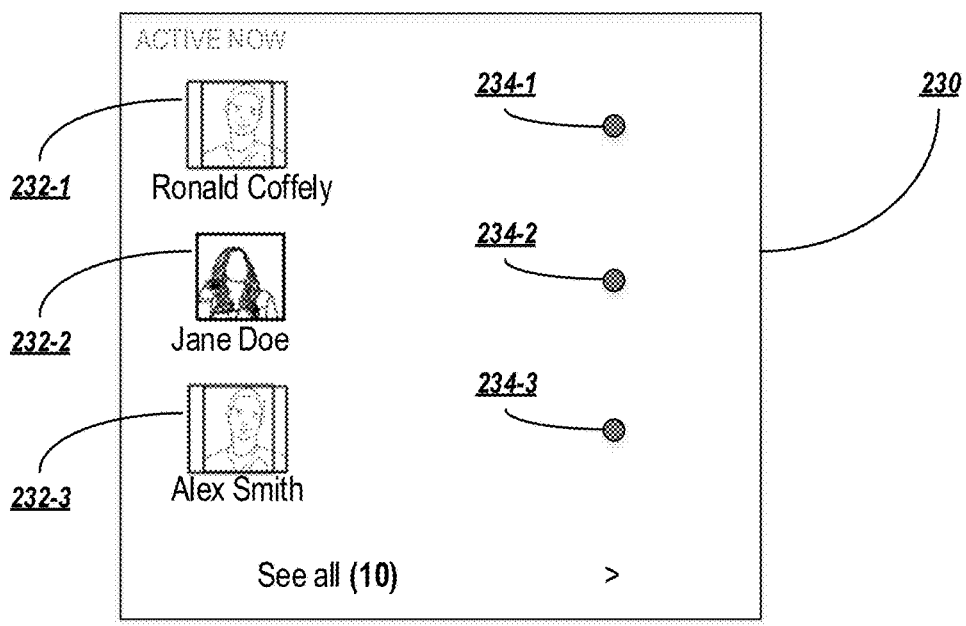
FIG. 2D depicts an example of a people/states module.

FIG. 2D depicts an example of a people/states module 228. The people/states module may display a list of the user's contacts who satisfy a condition that the contact be in one or more selected states. For example, the people/states module 228 may include a list of contacts 230 that are currently online, or who have recently participated in a conversation. The people/states module 228 may include an indicator 232 that indicates the current state of the associated contact 230. In the depicted example, the indicator 232 is a color-coded dot that changes color to reflect if the contact 230 is online or away.

The list of contacts in the people/states module 228 may be dynamically updated as contacts in the user's contacts list change their states, with contacts being added or removed from the people/states module. The people/states module may be configurable to allow the user to select how many contacts should be displayed in the people/states module, and in which state(s) the user is interested. If the people/states module 228 is configured to display a specific number of contacts that is less than the total number of contacts that match the selected states, then the people/states module 228 may apply one or more relevancy metrics to determine which contacts to display (e.g., contacts most recently messaged, contacts messaged at the highest frequency, etc.). The relevancy metrics may include the metrics described above in connection with the top contacts module.

Figure 2E:
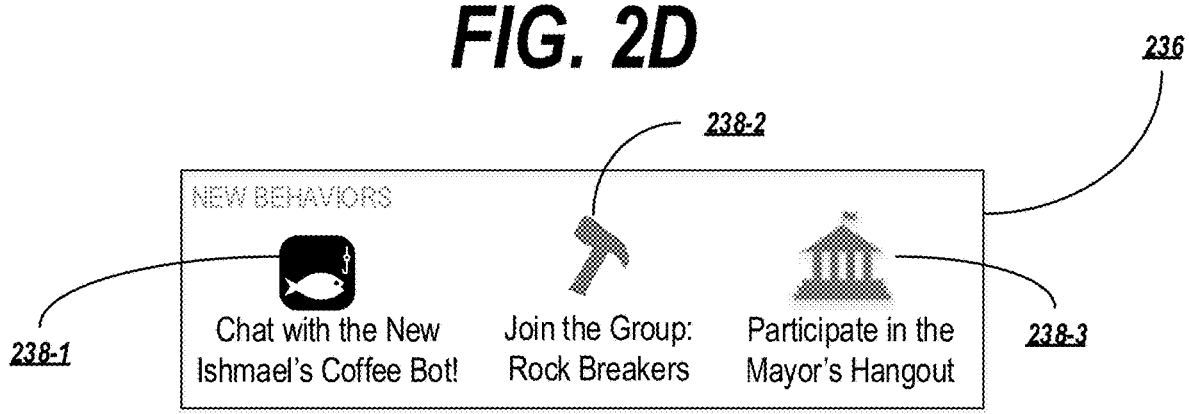
FIG. 2E depicts an example of a new behavior module.

FIG. 2E depicts an example of a new behavior module 236. The new behavior module 236 presents a list of behaviors or activities that the inbox owner could engage in on the messaging service, but for which the inbox owner has not (or has not recently) engaged. In the depicted example, the user is presented with the content option 238-1 to chat with a bot representing a company that the user likes or is predicted to like.

The new behavior module 236 may also or alternatively suggest behaviors in which the user does engage in some contexts, and for which the messaging service determines the user would be likely to engage if presented with the opportunity. For example, the user may have previously joined an interest group (e.g., "Rock Climbers of Springfield"), and the messaging service may determine that the user would be likely to want to join a related group. In the depicted example, the user is presented with a content option 238-2 to join the "Rock Breakers" group, representing another group of local rock climbers.

In a further example, the user may have previously participated in hangouts or online gatherings; when a celebrity or public figure begins a new hangout or gathering, the user may be presented with an option 238-3 to join the gathering in the new behaviors module 236.

In another example, if new functionality is added to the messaging service, then the new behavior module 236 may suggest that the inbox owner try the new functionality. One example of new behavior may be engaging in a video conversation—if the inbox owner has not previously engaged in a video conversation, but instead has always engaged in text messages, then the new behavior module 236 may suggest that the inbox owner initiate a video call with another user.

Figure 2F:
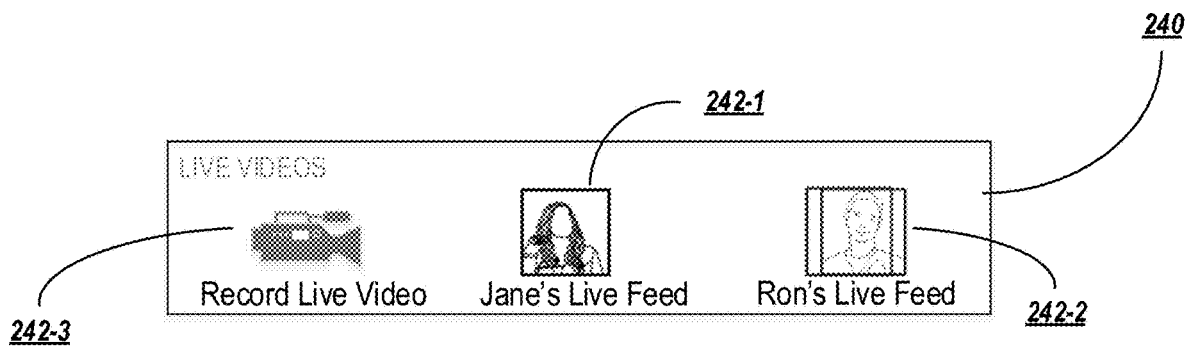
FIG. 2F depicts an example of a live videos module.

FIG. 2F depicts an example of a live videos module 240. The live videos module 240 may present content options 242-1, 242-2 representing live video streams currently being transmitted by other users of the messaging service (or an associated social networking service). The live videos module 240 may also present a content option 242-3 for allowing the inbox owner to create a live video stream from their device.

Figure 2G:
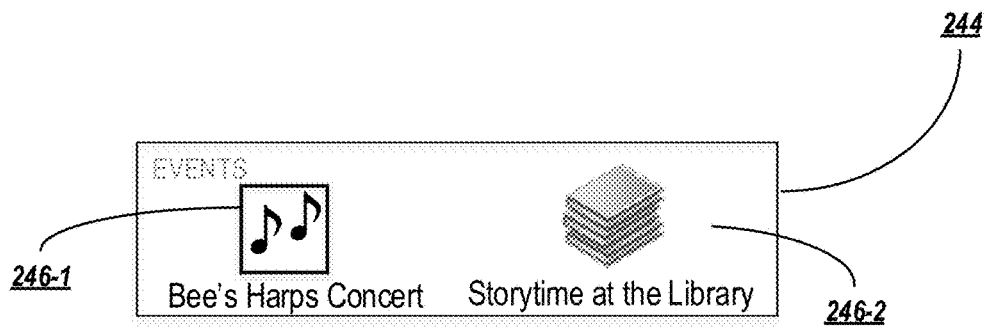
FIG. 2G depicts an example of an events module.

FIG. 2G depicts an example of an events module 244. The events module 244 may display a list of upcoming events 246 that the inbox owner and/or the inbox owner's contacts are scheduled to attend. Alternatively or in addition, the events module 244 may display a list of events 246 in which the messaging service or social networking service have determined the inbox owner may be interested (e.g., based on the inbox owner's interests as indicated through the inbox owner's interactions on a social network, or based on the interests of the inbox owner's contacts).

Figure 2H:
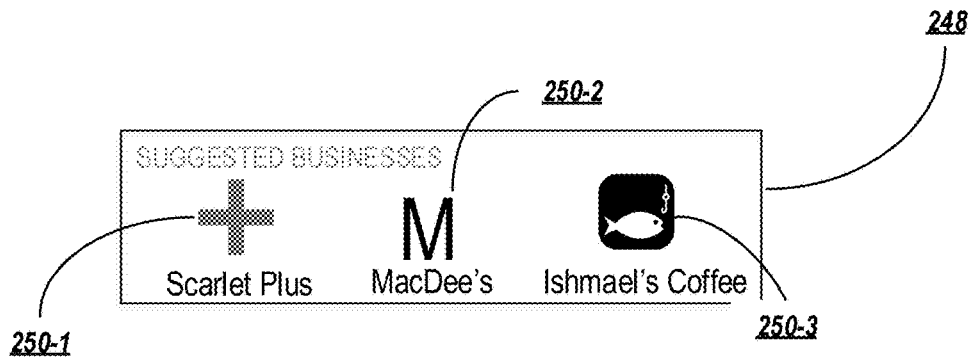
FIG. 2H depicts an example of a businesses module.

FIG. 2H depicts an example of a businesses module 248. The businesses module 248 may display a list of businesses 250 that the inbox owner and/or the inbox owner's contacts have previously interacted. Alternatively or in addition, the businesses module 248 may display a list of business 250 in which the messaging service or social networking service have determined the inbox owner may be interested (e.g., based on the inbox owner's interests as indicated through the inbox owner's interactions on a social network, or based on the interests of the inbox owner's contacts).

Figure 2I:
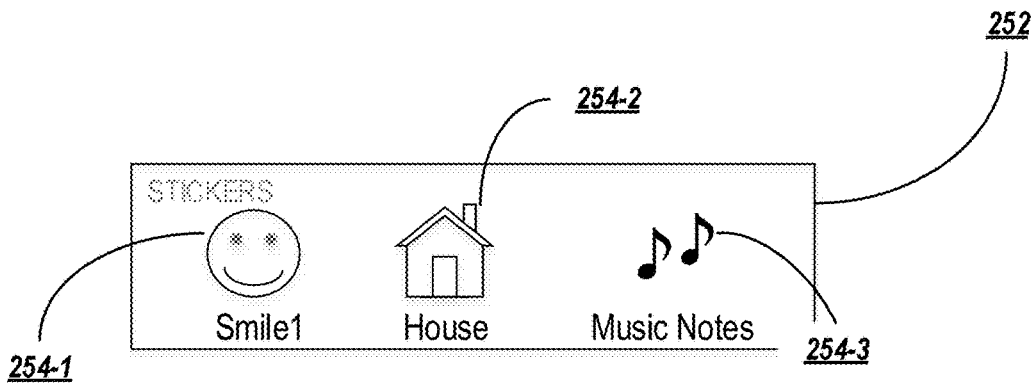
FIG. 2I depicts an example of a messaging stickers module.

FIG. 2I depicts an example of a messaging stickers module 252. The messaging service may allow the inbox owner to add graphics referred to as stickers to a message. These stickers may be downloaded from the messaging service, a social networking service, or another site. The stickers module 252 may display a list of stickers 254 for which the inbox owner may have an interest. The inbox owner may interact with the stickers module 252 in order to download or flag stickers for use in future messages. Upon selecting one or more of the stickers 254-*i*, the selected stickers may be downloaded and added to the user's local library for future use.

Figure 2J:
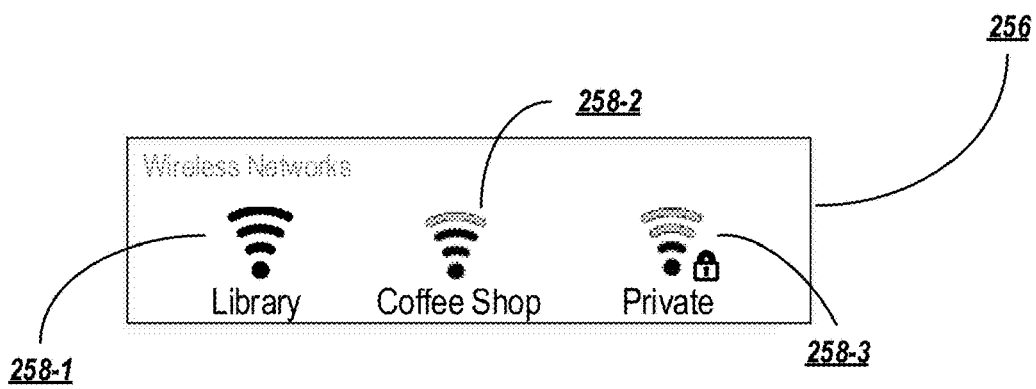
FIG. 2J depicts an example of a wireless network finder module.

FIG. 2J depicts an example of a wireless network finder module 256. The wireless network finder module 256 may display a list of available wireless networks 258 in proximity to the device of the inbox owner. The wireless network finder module 256 may also display information about the networks, such as the network name, the entity that provides or manages the network, wireless signal strength, and whether and how the network is secured. The inbox owner may select one of the wireless networks through the wireless network finder module 256 in order to connect to the wireless network.

Figure 2K:
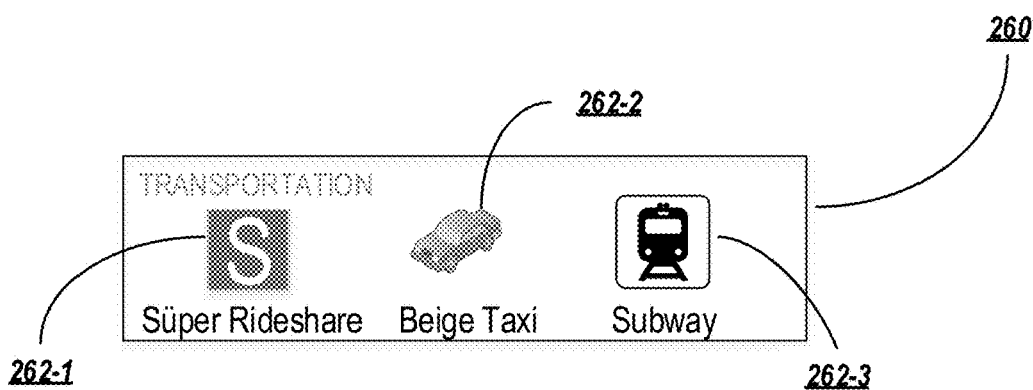
FIG. 2K depicts an example of a transportation services module.

FIG. 2K depicts an example of a transportation services module 260. The transportation services module 260 presents options for allowing the inbox owner to secure transportation, either immediately or at a scheduled time. The transportation services module 260 may display a list of transportation services 262 that are available in an area proximate to the inbox owner (as determined, for example, by the location of the inbox owner's mobile device). The transportation services may include, for example, taxi services, ride sharing services, public transportation, etc. The transportation services module 260 may connect to an application on the user's device, or to an internet site, for securing the transportation services. The transportation services module 260 may connect to a social networking page associated with a transportation service and may allow the user to communicate with the ride sharing service's page (e.g., through bot interaction). The transportation services module 260 may, alternatively or in addition, display a calendar allowing transportation services to be scheduled for a future time.

Any or all of the above-described modules may be displayed in the inbox interface (as well as additional modules described below). FIG. 3 is a flowchart depicting an exemplary process 300 for displaying an inbox interface including one or more modules.

At block 302, a messaging application may receive an instruction to display an inbox interface for a messaging service associated with the messaging application. Block 302 may occur, for example, in response to starting up the messaging application or in response to receiving an instruction to access a home screen or inbox screen in the messaging application.

At block 304, the inbox interface may be generated and a first set of messages may be displayed in a first portion of the inbox interface. The first portion of the inbox interface may provide thread display functionality, in which message threads are displayed. The message threads may be summarized in the first portion of the inbox interface (e.g., by displaying a thread's most recent message, or a representative message of the thread, and/or a list of participants in the thread). Interacting with one of the message threads may cause the message thread to be expanded so that an exchange between two or more thread participants may be viewed.

In some embodiments, the first portion of the interface may be provided as a module specifically dedicated to message or thread display functionality.

The first set of messages displayed in the first portion of the inbox interface may include a subset of the totality of the threads or messages available to the inbox owner, as determined based on a messaging cliff (discussed in more detail below). For example, the first set of messages may include a set of unread messages or a set of recent messages received within a predetermined amount of time.

In some embodiments, messages that are not selected for inclusion in the first set of messages may be collapsed into a message header and presented, e.g., at the end of the first set of messages.

At block 306, the inbox interface may receive an instruction to navigate past the first portion of the inbox interface. For example, the messaging application may register a gesture on a touch screen corresponding to a scrolling gesture, where scrolling the interface in accordance with the gesture would cause the interface to scroll beyond the final message or message thread in the first set of messages. Scrolling or navigation may be achieved in other ways as well, such as by interacting with a pointing device (e.g., a computer mouse), voice commands, etc.

At block 308, the messaging application may cause a second portion of the inbox interface to be displayed. The second portion may include one or more modules, where the modules of the second portion provide access to functionality that is different from the message or thread display functionality of the first portion of the inbox interface. As the inbox interface is scrolled through, the second portion of the inbox interface may incrementally or immediately replace the first portion of the inbox interface as the inbox interface is scrolled.

A list of the modules to display may be retrieved from a messaging server. The list may include a set of identifiers associated with each module to be displayed. Optionally, an entry in the list associated with each module may include further information, such as a type of the module, metadata such as a name of the module to be displayed, and optionally may include content items to be displayed. The content items returned with the list of the modules may be a null (empty) set, in which case the module may determine which content to display, either based on local content on the client device or remote content on a server associated with the module.

The messaging server may determine a subset of available modules to assign to the user (e.g., based on the user's predicted affinity for the modules) and may provide the list of modules to a client device running the inbox owner's messaging application.

The ordering of the modules in the second portion of the inbox interface may be determined by an inter-module ranking, as discussed in more detail below. In some cases, a module in the set of modules may be determined to be highly relevant, which may cause the module to be elevated in the inter-module ranking. In some embodiments, if it is determined that one of the modules in the set of modules is particularly relevant (e.g., above a certain relevancy threshold), then the module may be elevated even above the first portion of the interface (e.g., so that the module is displayed before the messages or message threads). For example, if a particular live video is being viewed by a significant number of the contacts of the inbox owner, then the live videos module may be elevated above the messages of the first portion of the interface.

The content within the modules may be retrieved from the messaging server associated with the messaging service. Alternatively or in addition, the content may be retrieved from separate servers associated with each module (e.g., each module may independently define and fetch its own content).

At block 310, the inbox interface may receive an instruction to navigate past the second portion of the inbox interface. For example, the messaging application may register a gesture on a touch screen corresponding to a scrolling gesture, where scrolling the interface in accordance with the gesture would cause the interface to scroll beyond a final module of the set of modules in the second portion of the interface. Scrolling or navigation may be achieved in other ways as well, such as by interacting with a pointing device (e.g., a computer mouse), voice commands, etc.

At block 312, the messaging application may optionally cause a second set of messages or message threads to be displayed in a third portion of the inbox interface. The third portion may be displayed after the second portion, and may incrementally or immediately replace the second portion of the inbox interface as the inbox interface is scrolled. The second set may include messages or message threads that were not flagged for inclusion in the first set of messages.

Alternatively or in addition, some or all of the second set of messages or message threads may be collapsed in the first interface portion, as described above.

Sharables Modules

A number of module types have been discussed above. In addition to these modules, a particular type of module configured to share local or social networking content may also be provided. Sharables modules are described in detail with reference to FIGS. 4A-4G.

Figure 4A:
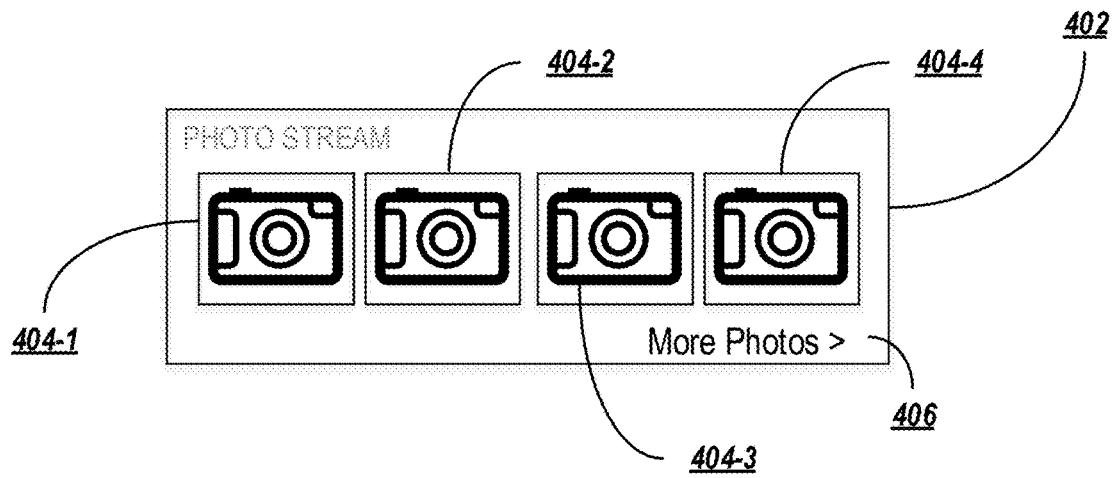
FIG. 4A depicts an example of a sharing module for sharing local content.

FIG. 4A depicts an example of a local sharing module 402 for sharing local content. A number of local content items 404 may be displayed in the sharing module 402. The local content items 404 may be, for example, photos or videos from a local device on which the messaging application is running.

The local sharing module 402 may display a predetermined or dynamically determined number of local content items 404 on the display. More local content items 404 may be accessible, for example using a horizontal scrolling technique or through an additional menu 406. Activation of the menu 406 may, for example, cause the local sharing module 402 to present an interface into the local storage of the device. The messaging application may, for example, access the photo album of the local device and suggest photos or videos that the inbox owner may be interested in sharing with their contacts.

Figure 4B:
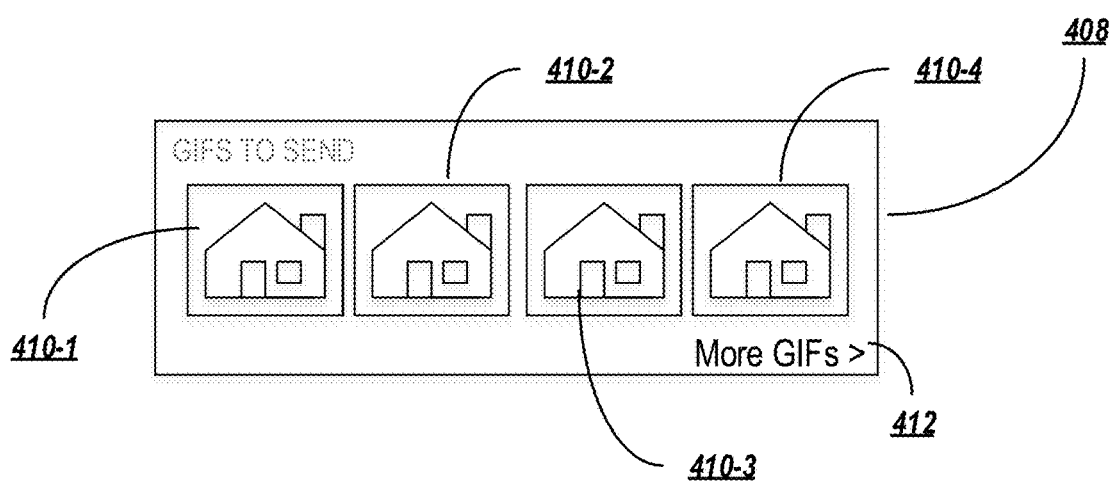
FIG. 4B depicts an example of a sharing module for sharing social networking content.

FIG. 4B depicts an example of a social media sharing module 408 for sharing social networking content. The social media sharing module 408 may retrieve content items 410 associated with the inbox owner from a social networking service. For example, the content items 410 may include media that has been uploaded by the inbox owner to the social networking service, media that the inbox owner has interacted with through the social networking service (e.g., content on which the inbox owner has commented, liked, etc.), or media that the social networking service determines that the inbox owner is likely to appreciate or enjoy. The content items 410 may include, for example, videos, pictures (e.g., GIFs), articles, etc. that have been uploaded to, or otherwise accessed from, the social networking service.

Additional content items 410 may be available through a horizontal scrolling technique. Alternatively or in addition, a menu 412 may be provided for displaying additional content items 410. Activation of the menu 412 may, for example, cause the social media sharing module 408 to present an interface into the social networking service and display additional content items 410 available through the social networking service.

Figure 4C:
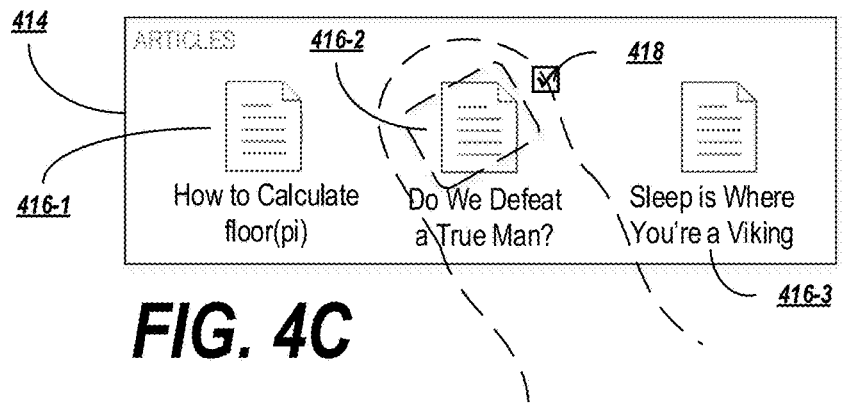
FIG. 4C depicts an exemplary interface for selecting content to be shared.

FIG. 4C depicts an exemplary interface 414 for selecting content to be shared. The content may be local content as shown in the local sharing module 402 or content from a social networking service as shown in the social media sharing module 408. In the depicted example, the content items 416 in the interface 414 represent articles available on a social networking service.

As shown in FIG. 4C, one or more of the content items 416 may be selected. The selected content items may be identified using an identifier 418, such as a checkmark in this example. Once one or more of the content items 416 are selected, a recipients interface may be displayed, as shown in FIG. 4D.

Figure 4D:
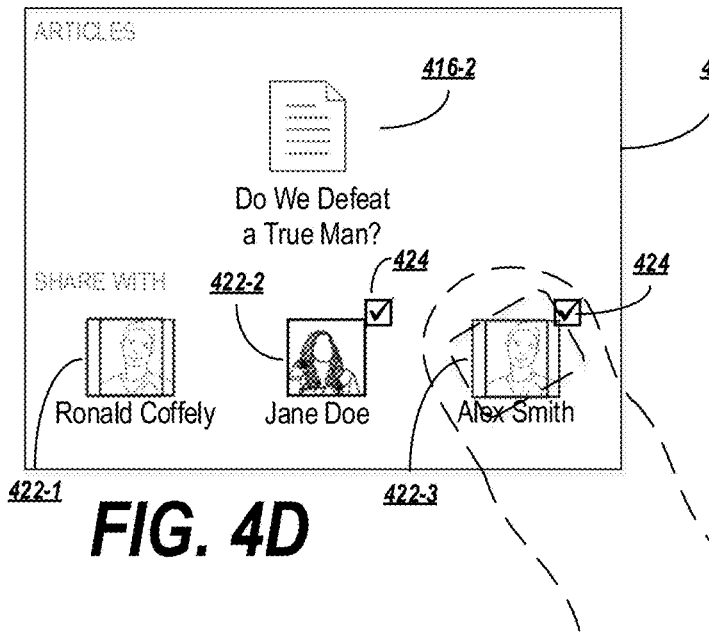
FIG. 4D depicts an exemplary interface for selecting a group of recipients to receive the content selected in FIG. 4C.

FIG. 4D depicts an exemplary interface 420 for selecting a group of recipients 422 to receive the content selected in FIG. 4C. The recipients 422 displayed in the interface 420 may include users connected to or associated with the inbox owner through a social networking service or through the messaging service. For example, the recipients 422 may include recipients with whom the inbox owner has recently shared content items, or whom the inbox owner has recently messaged. The recipients 422 may be selected, at least in part, based on an identity of the content items 416 selected for sharing. For example, the social networking service may identify a subset of the inbox owner's contacts or friends on the social networking service who (based on their own content interaction history) the social networking service determines are likely to enjoy or appreciate the content items 416. To accomplish this, the social networking service may consult a social graph, as described in more detail below.

Upon selecting one or more of the recipients 422, an indication 424 (such as a check box, in this example) may be displayed to indicate which recipients 422 have been selected. The messaging application may then display an interface for confirming the sending of the content to the recipients, such as the exemplary interface 426 depicted in FIG. 4E.

The interface 426 may display the selected content items 416 and the selected recipients 422 from the interfaces 414, 420. Thus, the inbox owner may review the content to be distributed and the users to whom the content will be shared. Optionally, a prompt may be provided for allowing the inbox owner to add explanatory text when the content is sent.

When the inbox owner is satisfied, a confirmation indicator 428 may be selected to confirm the transmission of the content. When the indicator 428 is selected, the messaging application may transmit the selected content items 416 to the selected recipients 422.

Figure 4E:
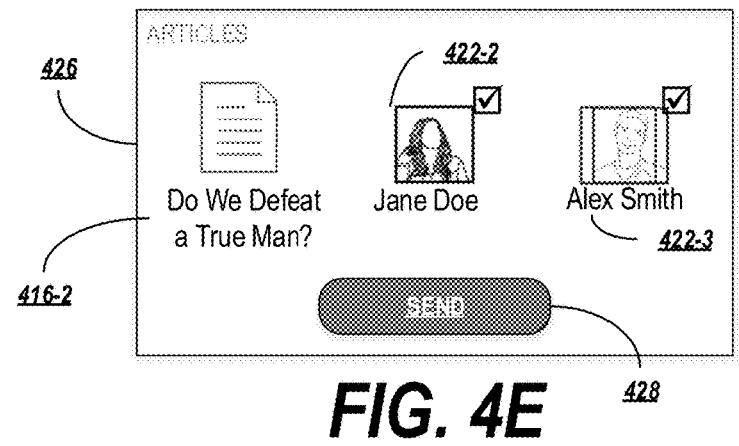
FIG. 4E depicts an exemplary interface for confirming the sending of the content to the recipients.
Figure 4F:
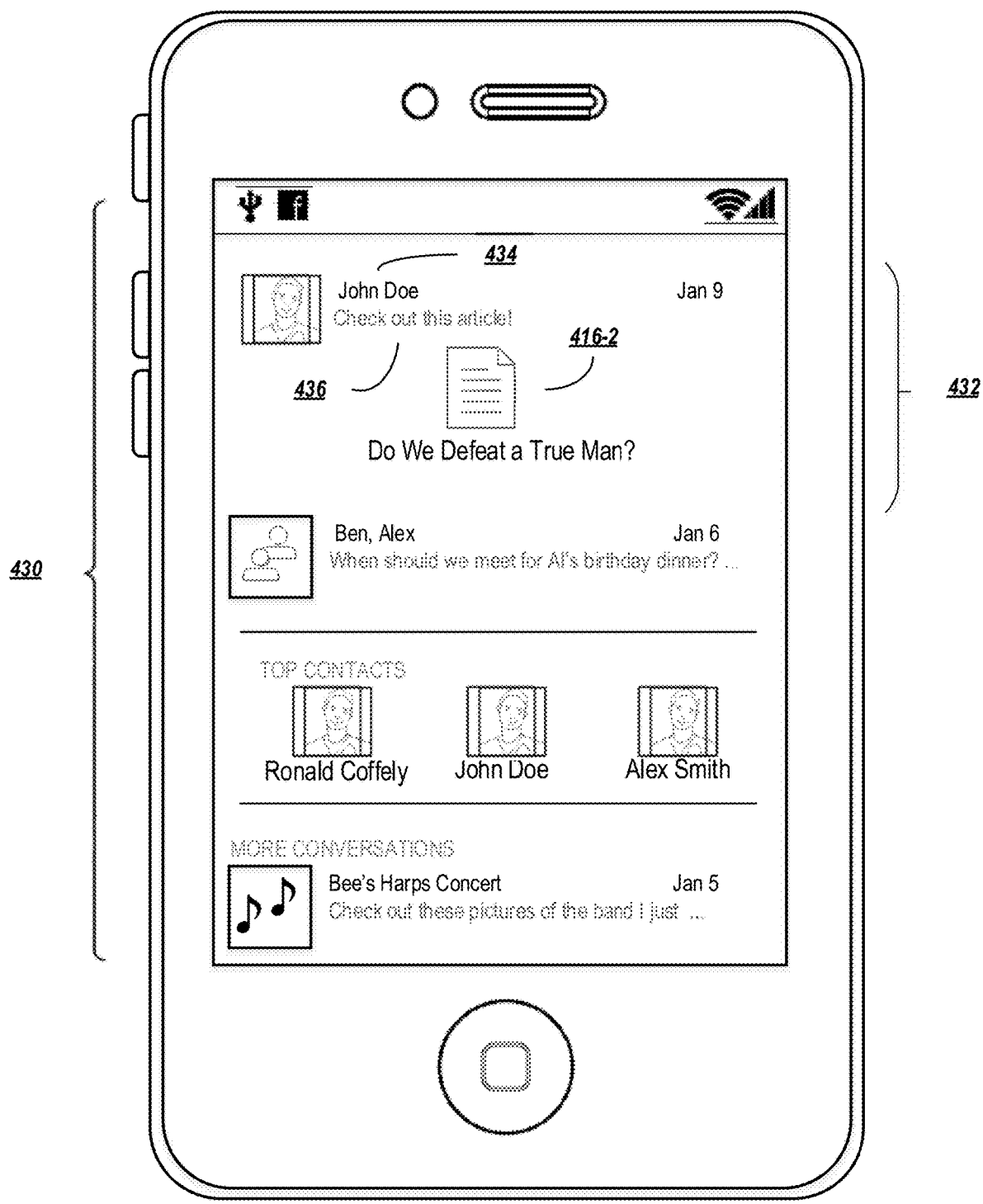
FIG. 4F depicts an exemplary inbox after receiving the content shared in FIGS. 4C-4E

FIG. 4F depicts an exemplary inbox interface 430 for one of the recipients 422, after receiving the content 416 shared in FIGS. 4C-4E. A new message thread or inbox item 432 may be created in the first section of the modular inbox (e.g., the section containing message or thread content). The inbox item 432 includes an identification 434 of the sender of the content, along with any explanatory text 436 added during the sending process. The shared content item 416 may be displayed in the message, and interacting with the shared content item 416 may cause the inbox interface 430 to display a larger version of the content item 416 (e.g., replacing a thumbnail of the content item 416 with a larger version), or to navigate to a location of the content item (e.g., taking the recipient to the recipient's social networking page, in the case of social networking content, or to a web site containing the content).

Figure 4G:
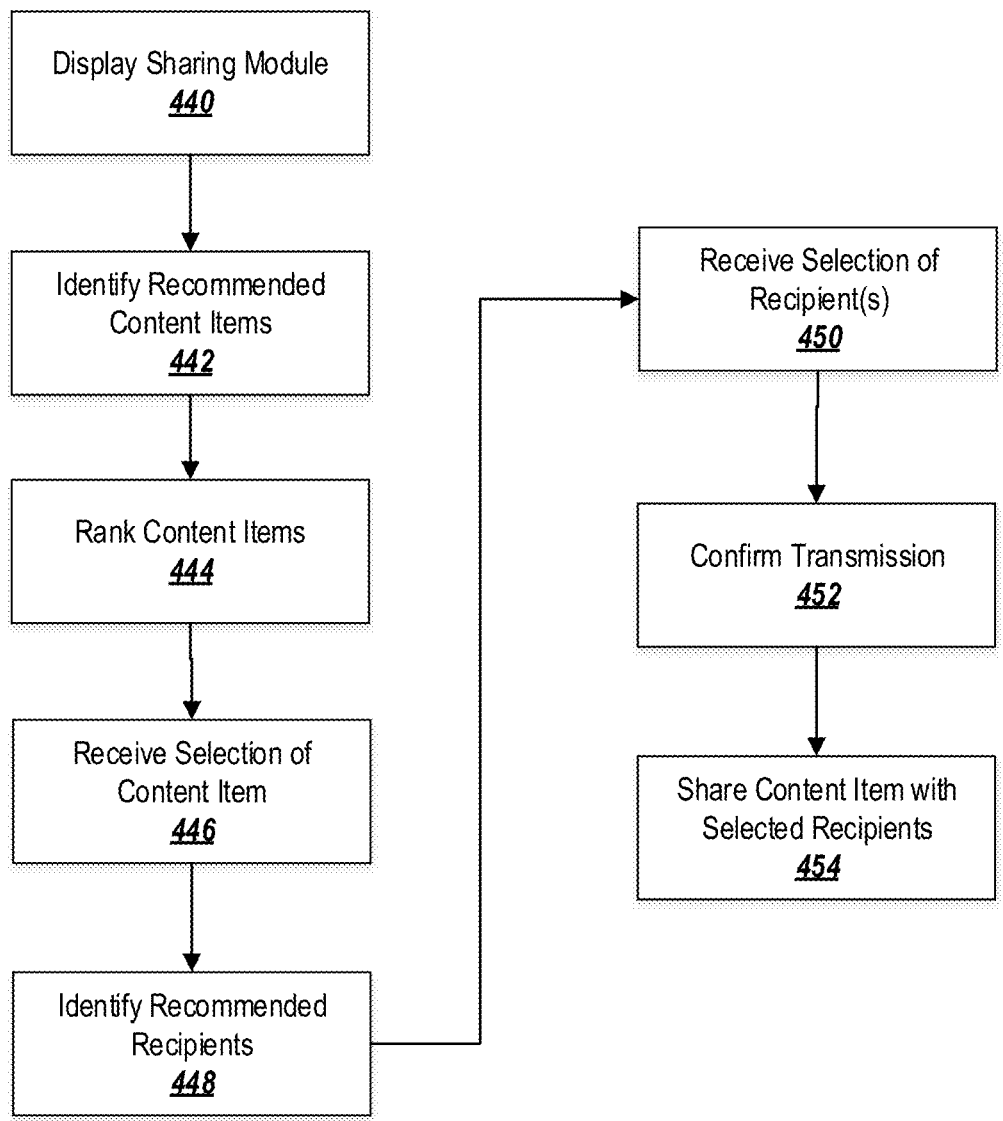
FIG. 4G is a flowchart depicting an exemplary process for sharing content from a module.

FIG. 4G is a flowchart depicting an exemplary process 438 for sharing content from a module.

At block 440, the messaging application may display a sharing module. The sharing module may be displayed in the second portion of the modular inbox, dedicated to non-message or non-message-thread display. In some embodiments, the module may be configured to share content from a social networking service with users of the messaging service. In other embodiments, the module may be configured to share local content from the local device with users of the messaging service. The module may be distinct from a portion of the inbox interface that provides message or message thread display functionality;

At block 442, the messaging application may identify recommended content items for display. The sharing module may be a module for sharing a particular type of content, such as articles, videos, or pictures, and the messaging application may identify content of the type associated with the sharing module. The sharing module may define where content items for the sharing module may be found (e.g., a photo album or roll on the local device for a photos module, a social networking service for a videos module, etc.). The messaging application may retrieve a number of the content items (e.g., a number defined by the sharing module) from the identified location, and may select a recommended subset of the retrieved items for display.

The recommended subset may be determined based on one or more metrics, which may be defined by the sharing module. For example, in the case of a sharing module for sharing photos, the recommended items may be the most recently captured photographs on the local device. In the case of a sharing module for sharing content from a social network, the metrics may be based on consumption information for the content items. For instance, the most consumed or interacted-with content items on the social network may be selected as recommended content items. The recommendation may also be based on a determination of which content items the inbox owner is most likely to wish to share (e.g., which content the inbox owner has interacted with recently, or is likely to enjoy based on the inbox owner's interaction history through a social network).

At block 444, the content items identified in block 442 may be ranked. The content items may be ranked, for example, based on the recency of the content item, a predicted likelihood that the inbox owner would enjoy the content item, an amount time spent watching the content by the inbox owner or users associated with the inbox owner, etc. One or more ranking metrics may be defined by the sharing module. After the content items have been ranked, the sharing module may display the content items in ranked order.

At block 446, the sharing module may receive a selection of one or more content items to be shared. For example, the messaging application may register a touch at a location on a touch-sensitive display corresponding to the content item. The messaging application may register a selection in other ways, such as through a pointing device, voice commands, etc. The messaging application may update the display to show an indication (e.g., a check box) on the selected content item.

At block 448, a recommended list of recipients may be identified and displayed. The recommended list of recipients may be a subset of the inbox owner's contacts through the messaging service or social networking service.

The recommended list of recipients may be selected based at least in part on an identity of the content item. For example, a social networking service associated with the networking service may be consulted to determine which users are most likely to enjoy the content item (e.g., based on the users' consumption history through the social network and/or based on the users' likes and dislikes as indicated through the social graph). In some embodiments, the content item may be associated with one or more users, who may be identified as recommended recipients. For example, a photograph may include the inbox owner and may also include another member of the messaging service or a social networking service. The other users in the photograph may be selected as recommended recipients.

Alternatively or in addition, the messaging application may present an option for selecting a set of recipients not in the list of recommended recipients. For example, a menu item may be presented allowing the inbox owner to access their contacts list, and recipients may be selected from the contacts list.

At block 450, the sharing module may register a selection of one or more recipients presented in block 448. For example, the messaging application may register a touch at a location on a touch-sensitive display corresponding to the recipient. The messaging application may register a selection in other ways, such as through a pointing device, voice commands, etc. The messaging application may update the display to show an indication (e.g., a check box) on the selected recipient.

At block 452, the messaging application may present a prompt asking the sender to confirm transmission of the selected content item(s) to the selected recipient(s). The messaging application may optionally allow the sender to add a message to the content item for transmission to the recipients. Upon receiving confirmation of the sender's intent, at block 454 the messaging application may share the identified content with the identified recipients. For example, the messaging application may generate a message and/or message thread including the content item and the sender's message (if any). The messaging application may transmit the message to the recipients identified at block 450 using the messaging service.

Promotional Material Delivery

Another type of module and/or content item that may be employed in the modular inbox is a promotional material module or content item. FIGS. 5A-5D depict various examples of promotional material delivery.

Figure 5A:
FIG. 5A depicts an example of a promotional material module.

FIG. 5A depicts an example of a promotional material module 502. The promotional material module 502 may be a module dedicated to providing promotional material, such as sponsored items. Promotional content items 504 such as advertisements, offers, discounts, etc. may be displayed in the promotional material module. The promotional content items 504 may be selected dynamically, such as by determining a location of the client device and selecting promotional content items 504 associated with stores or shops located in close proximity to the client device.

The exemplary promotional material module 502 of FIG. 5A includes two different types of promotional material. A first promotional content item 504-1 is a sponsored advertisement prompting a user to purchase a good or service. A second promotional content item 504-2 is a discount offer that provides the user with an opportunity to receive goods or services for free or at a discount. Thus, the first content item 504-1 is a sponsored advertisement while the second promotional content item 504-2 is a discount offer that provides a benefit to a user. The messaging application may treat these different types of promotional content differently, such as by surfacing the promotional content items 504 in different ways depending on whether the content item is an advertisement or a discount offer.

For example, advertisement content may be surfaced only when a user is in close proximity to the goods or services being advertised, whereas a discount offer may be displayed at any time. A user may interact with the promotional content item 504 associated with the discount offer to claim the discount offer and generate a message related to the discount offer. At a later time, the user can interact with the message in order to activate the discount at a retail location.

Figure 5B:
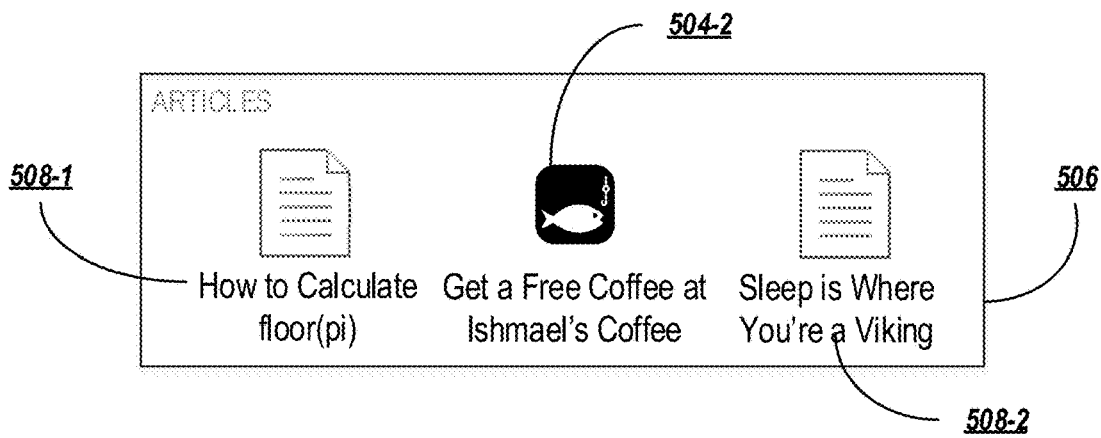
FIG. 5B depicts an example of promotional material integrated into non-promotional material module.

In another embodiment, advertisements may be relegated to a dedicated promotions module 502, whereas discount offers may be interspersed among the content of other modules. For example, FIG. 5B depicts an example of promotional material integrated into non-promotional material module 506.

In this example, the module 506 is a sharing module for sharing articles from a social networking service. The content items of the sharing module include various sharable content items 508 in the form of articles. A promotional content item 504-2 in the form of a discount offer is provided among the sharable content items 508. The intra-module rank of the promotional content item 504-2 (defining where in the module the item 504-2 will appear) may depend on a level of sponsorship by the promoter of the promotional content item 504-2.

In some embodiments, advertisements may also be interspersed in non-promotional materials module. For example, depending on an amount of sponsorship by the promoter, the promotional content items may be displayed higher in the intra-module ranked order, or may be displayed in a non-promotional content module. In another embodiment, the module in which sponsored content is provided may be elevated in an inter-module ranked order depending on the level of sponsorship.

In some embodiments, a user may be presented with an option to share a discount offer with their friends, e.g. to encourage the user and their friends to gather together at a given location in order to claim the offer.

Figure 5C:
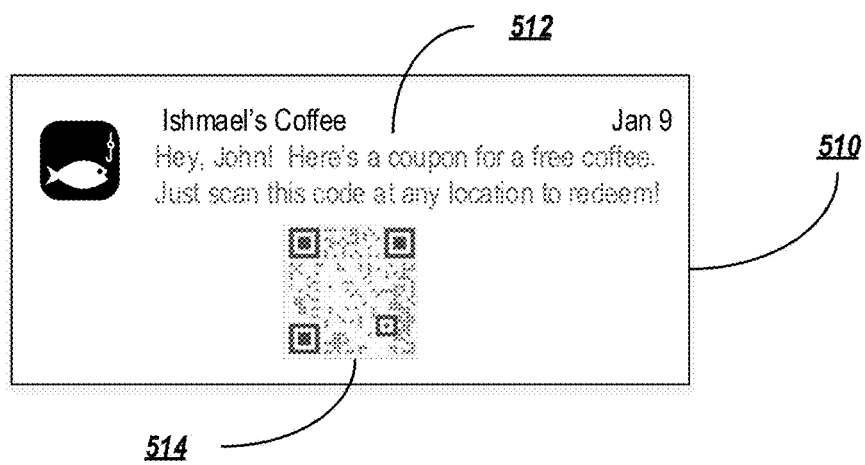
FIG. 5C depicts an example of a message generated in response to interacting with promotional material.

As noted above, in some embodiments a user may interact with the promotional content item 504 associated with the discount offer to claim the discount offer and generate a message related to the discount offer. FIG. 5C depicts an example of a message 510 generated in response to interacting with promotional material.

The message 510 may appear as any other message among the user's message threads, and may be treated as any other message content for purposes of the modular inbox. The message 510 includes message text 512 generated by a promoter of the promotional content item 504 which describes the offer being sent. Optionally, the message 510 may also include a scannable code 514, such as a bar code or QR code, which a user may present at a retail location in order to claim the offer or discount. In the depicted example, scanning the code 514 at a retail location results in the user being able to claim a free coffee.

FIG. 5D is a flowchart depicting an exemplary process 516 for providing promotional content in a module.

At block 518, the messaging application may display a first set of messages in a first portion of an inbox interface for a messaging service. The first portion of the inbox interface may be dedicated to, or may primarily provide, message or thread display functionality. The first portion of the inbox may end at a messaging cliff, as described in more detail below.

At block 520, the messaging application may receive an instruction to navigate past the first portion of the inbox interface. For example, the messaging application may register a gesture on a touch screen corresponding to a scrolling gesture, where scrolling the interface in accordance with the gesture would cause the interface to scroll beyond the final message or message thread in the first set of messages. Scrolling or navigation may be achieved in other ways as well, such as by interacting with a pointing device (e.g., a computer mouse), voice commands, etc.

At block 522, the messaging application may select promotional material for display. For example, the messaging service may maintain a database or other storage of promotional material, and the messaging application may access the database in order to retrieve a number of candidate promotional materials. To determine which of the candidate promotional materials to display, the messaging application and/or a server of the messaging service may apply one or more metrics, such as: a history of interaction between the user and the promoter on the messaging service, a social networking service, or elsewhere; a determined likelihood that the user will find an offer from the promoter desirable; or a proximity of the user to a retail location associated with a promotion, among other possibilities.

In an embodiment employing a proximity metric, block 522 may involve detecting a location of a mobile client of a user of the messaging service, and selecting the promotional material based on a proximity of the mobile client to a location associated with a source of the promotional material, such as when the location is determined to be within a predetermined distance from the source.

According to some embodiments, block 522 may involve determining if the candidate promotional material is an advertisement or a discount offer; and selecting a presentation technique for the promotional material depending on whether the promotional material is the advertisement or the discount offer, as described above.

At block 524, the messaging application may display a module in a second portion of the inbox interface. The module may include some or all of the promotional material selected at block 522. The module may be distinct from the first portion of the inbox interface that provides the message or message thread display functionality.

In some embodiments, the module may be configured to exclusively share promotional material with a user of the messaging service. In other embodiments, the module may be dedicated to other messaging service functionality, where the functionality is distinct from functionality for displaying promotional material. In other words, the promotional material may be integrated into other, non-promotional modules, with the promotional material being presented alongside other content of the module. For example, in the "People/States" module, the inbox interface may present a number of friends (e.g., the user's mother, the user's friend, etc.) alongside a promoted content item (e.g., a phone company's customer service representative, which could be a bot).

The module containing the promotional content may be one among several modules that are presented in a ranked order. Depending on a level of sponsorship of the module containing the promotional content, the ranked order may be altered. For example, if the sponsors who provided promotional content in the module provide a sufficiently high level of sponsorship (above a threshold amount), the module may be elevated higher than other modules in the modular inbox.

At block 526, the messaging application may receive a selection of promotional material. Depending on the actions defined by the promoter who provided the promotional material, a number of different actions may be taken. For example, interacting with the promotional material may take the user to a web page or social networking site associated with the promoter.

In some embodiments, interacting with the promotional material may cause a message to be generated (block 528). Based on instructions provided with or associated with the promotional content item selected, message content (potentially including a scannable code) may be automatically generated and transmitted to the inbox owner through the messaging service. The inbox owner may be provided with an option to share the promotional content and/or the generated message with other users.

The Cliff

The above-described modules may be displayed after a first subset of the inbox owner's messages in the modular inbox. The cut-off location after which the inbox transitions to modules, rather than messages or message threads, is referred to herein as the cliff. FIG. 6 is a flowchart depicting an exemplary process 600 for determining a transition point (cliff) between a first group of messages and a set of one or more modules.

At block 602, the messaging application may receive an instruction to display an inbox interface for a messaging service. Block 602 may occur, for example, in response to starting up the messaging application or in response to receiving an instruction to access a home screen or inbox screen in the messaging application.

At block 604, the messaging application may determine a number of messages to be displayed in a first portion of the inbox interface containing a subset of the messages. The subset may be a number of messages that is smaller than the totality of all of the messages available in the user's inbox. In some embodiments, the number may fall between a lower threshold for the number of messages threads and an upper threshold for the number of messages.

The lower threshold may be a predetermined minimum number of messages/threads. For example, it may be undesirable to display too few messages before non-message content is displayed. Thus, the predetermined minimum may be set to a value (e.g., 2-6 message threads) so that at least a certain number of message threads are displayed prior to non-message content. In some embodiments, the minimum number of messages/threads may be dynamically determined using criteria similar to that discussed below.

The upper threshold may be predetermined, or may be dynamically determined. The upper threshold (and the criteria used to determine the upper threshold) may vary from user to user.

For example, at block 606, the messaging application may dynamically select an upper threshold based on one or more criteria. The criteria may include, for example, whether the user has participated in at least a predetermined number of conversations over a predetermined period of time. For example, if the user is not particularly active, the maximum number may be set relatively low (as the user likely only needs to see a few of the most recent conversations). On the other hand, if the user is highly active, the user may have a number of message threads in which they are currently participating, and is likely to wish to see these threads at the forefront in the messaging application.

Another criterion may be the number of message threads in which there is a currently active conversation (e.g., a conversation in which the most recent message has been received in less than a predetermined threshold amount of time), and/or the number of message threads having unread messages. In some embodiments, the upper threshold may be set such that the first portion of the inbox interface shows all of the threads that include an active conversation and any threads that have unread messages. The last message to meet either of these criteria may be selected to define the upper threshold.

Another example of a criteria may be historical interactions with the messaging application. For example, if a user utilizes the messaging application multiple times per day may wish to see more conversations than a user who utilizes the messaging application on a limited basis.

Another example of a criteria is the current time of day. If the current time is during the night hours, the user is likely asleep and not messaging particularly actively. Thus, the system may select a relatively small upper threshold. On the other hand, during the day the threshold may be increased since the user is likely to be relatively more active.

Yet another example of a criteria is the amount of time since the last active conversation. For example, the messaging application may determine the last thread in which a user had an active conversation in the previous n number of hours (e.g., n=6, 8, 24, etc.). The upper threshold may be set to encompass the number of active message threads within the time window.

The criteria may be combined with each other. For example, the messaging application may use the historical interaction information for the messaging application to alter the time window for the amount of time since the last active conversation. If the user is highly active with the messaging application, the time window may be set relatively short (e.g., 6 hours or even less), which would likely still result in a large number of conversations for an active user. On the other hand, an inactive user might have their time window set relatively long (e.g., one week), because the longer list of conversations may remind the user to follow up with people from several days ago, thus prompting the user to higher levels of activity. In another example, if the current time of day is during the user's work hours, the time window may be increased or decreased depending on whether the user actively uses the messaging service for work or not. A user actively using the messaging service for work may wish to see a relatively small number of the most recent messages, whereas a user that does not use the messaging service may wish to see a larger number of messages encompassing those which the user missed while at work.

In another embodiment, the number of unread messages and/or active conversations may be combined with the above-described time window. For example, the messaging application may determine the number of unread messages/ active conversations within the previous n hours. The upper threshold may be set to encompass these messages and conversations.

If there are no unread messages or active conversations within the time period, then the lower threshold determined at step 604 may be utilized.

At block 608, the messaging application may display the first set of messages (i.e., the number of most-recent messages and/or threads that do not exceed the lower threshold or the upper threshold, whichever is higher) in a first portion of the inbox interface. Optionally, the messages of the first set of messages may be displayed, but previously-read messages and/or messages without an active conversation may be filtered out and moved to the second subset of messages.

At block 610, the messaging application may display non-message content in a second portion of the inbox interface. The second portion may include a number of modules related to functionality of the messaging service that is not directly related to message or thread display functionality, such as the modules described in connection with FIGS. 2A-5D.

At block 612, the messaging application may display the second subset of messages. The second subset of messages may be displayed as a result of an instruction to navigate past the modules displayed in block 610. Following these modules, an additional message inbox may be displayed including the previously undisplayed messages/threads. In another embodiment, the messages of the second subset may be collapsed into a menu in the first portion of the inbox, as previously described.

Module Ranking

When two or more modules are displayed, an inter-module order may be established to define the display order for the modules (e.g., should the Top Contacts Module be displayed before the Photos Module?). If, for example, the user's mother recently came online, then this information may be particularly pertinent and the People/States Module may be a good candidate for an early spot among the modules. On the other hand, if a particular article is being widely shared on the user's social networking service, then a sharing module for sharing articles may be elevated to a top spot.

It is noted that the first portion of the display, including the first subset of the messages/message threads, may be treated as a module and may be ranked among the other modules for display. In some embodiments, the messages/threads module may be locked to the top of the inbox interface, although in other embodiments it may be allowed to float among the other modules depending on its rank. In some embodiments, the messages/threads module may be locked to the top slot unless another module is determined to be extremely relevant (e.g., the probability of interaction described in connection with FIGS. 7A and 7B is above a predetermined relatively high threshold), in which case the extremely relevant module may be elevated above the messages/threads module.

The inter-module order may be determined based on a dynamically calculated inter-module ranking. FIGS. 7A-7B describe how the inter-module ranking is determined, while FIG. 7C describes how content within a module may be ranked.

Figure 7A:
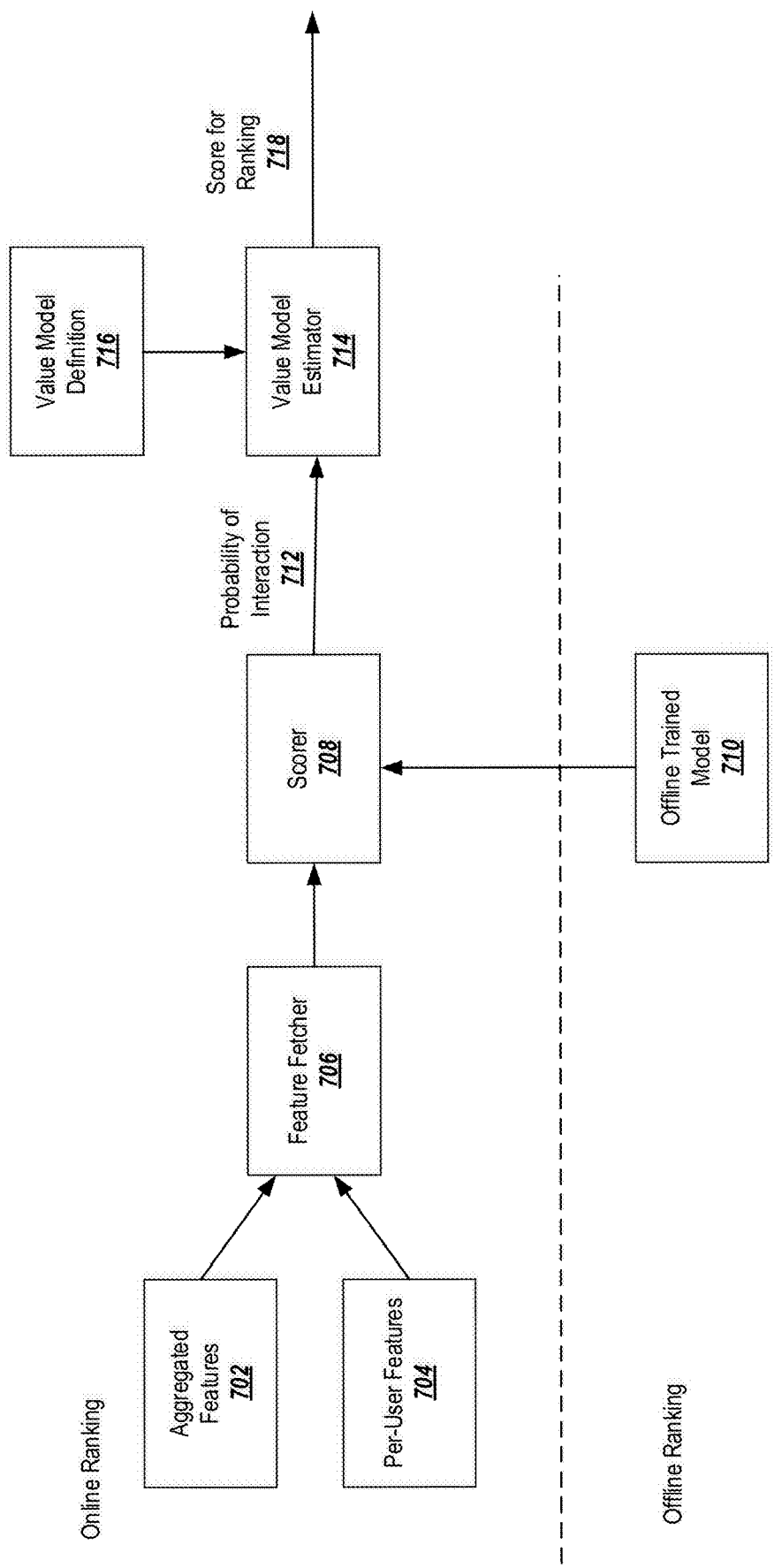
FIG. 7A is a block diagram providing an overview of a module ranking framework.

FIG. 7A is a block diagram providing an overview of a module ranking framework. Generally speaking, the module ranking framework proceeds in two stages. First, the framework determines how likely a person is to interact with the module in question. Second, the framework determines a value of providing the module to the messaging service. The probability is combined with the value to determine the module's rank score. The scores of different modules are compared to each other in order to determine the modules' ordering. In some embodiments, only modules above a predetermined threshold rank score are presented to a user in the second portion of the inbox interface.

The framework may evaluate a number of aggregated features 702 and a number of per-user features 704. The aggregated features 702 may use a user base (e.g., the messaging service's or a social networking service's user base) as a proxy for the currently-evaluated user, in order to evaluate the module's general popularity. The aggregated features 702 may include data regarding module usage as aggregated over the user base. For example, the aggregated features 702 may include the number of impressions of a given module in a predetermined period of time (e.g., 30 days) among the user base, the number of times the user base has interacted with the module in a predetermined period of time (e.g., 30 days), etc.

The per-user features 704 may include similar information, but may be specific to the user under evaluation (or may otherwise be generated on a per-user basis). For example, the per-user features 704 may include a number of impressions of a module for a given user-module pair, a number of interactions with a module for a given user-module pair, etc.

The aggregated features 702 and the per-user features 704 may be retrieved by a feature fetcher 706 for evaluation. The feature fetcher 706 may be, for example, a component of a server that retrieves the features from the messaging service and any applicable module providers. The feature fetcher 706 may aggregate the features and provide the features to a scorer 708.

The scorer 708 accepts the features as input and determines a probability of interaction 712 for the modules described by the features. The probability of interaction 712 may represent a likelihood that a given user (or a user in general) will use the module.

The scorer 708 may be supplemented by one or more offline trained models 710 that may improve the scorer's 708 predictions in certain contexts. For example, the offline trained models 710 may account for variables such as a user's age group, a user's gender, the user's recent posts to a social networking service, etc.

The scorer may determine the probability of interaction 712 according to a formula, such as the one described below in Equation 1:

$$\text{Probability of Interaction} = \lambda * \frac{\text{\# unit clicks by user} + 1}{\text{\# unit impressions by user} + 2} + (1-\lambda) * \frac{\text{\# unit clicks} + 1}{\text{\# unit impressions} + 2}$$

Equation 1

Where λ is a personalization multiplier which balances the user's behavior and the user base's aggregated behavior. One of ordinary skill in the art will recognize that Equation 1 is exemplary only, and that other suitable formulae may be used to estimate the probability that a user will interact with a module.

The determined probability of interaction 712 may be provided to a value model estimator 714. The value model estimator 714 may determine a value of the module to the messaging service or an associated social networking service. For example, it may be more valuable to the messaging service for the current user to start a new thread with another user (thus encouraging both users to become more active) than for the user to share an article with an already-active user, or for the user to view an advertisement. Thus, the messaging application may elevate the People/States Module above a Sharable Articles Module or a Promotional Materials Module.

To this end, the value model estimator 714 may consult a value model definition 716 that provides values for each of the modules accessible through the messaging service. The values provided by the value model definition 716 may be combined with the probability of interaction 712 to determine a final score for ranking 718 for each module. The scores for the modules may be compared to each other to determine relative ranks for the modules.

The above-described framework may be employed in an exemplary process 720 for determining an inter-module rank. FIG. 7B depicts an example of such a process 720.

At block 722, the messaging service may identify a first module and second module available for display by a client's messaging application. The first module and the second module may provide access to functionality of the messaging service that is distinct from message or thread display functionality.

At block 724, the messaging service may determine probabilities of interaction for the first module and the second module, such as the probability of interaction 712 discussed in connection with FIG. 7A. The probabilities of interaction may represent a likelihood that the inbox owner will use the first module and the second module, respectively.

As an alternative or in addition to the probability of interaction 712 as calculated n FIG. 7A, each module may provide its own estimation of the likelihood that the inbox owner will use the module. For example, each module may provide a number that reflects the quality of content currently available through the module (e.g., the quality of the content today as compared to the average day).

The probability of interaction may be augmented or may take into account other criteria, such as recency. For example, if a user takes a photo with their mobile device and then immediately accesses the messaging application, there may be an elevated likelihood that the user wishes to share the recently captured photograph with their messaging contacts. In another embodiment, the messaging application (or a related social networking service) may identify one or more other users in the photo, and may determine if the current user and the other users are highly connected or are highly likely to message each other. Such a coefficient may be used to elevate the priority of a module for sharing the photo, if other highly connected users are available through the messaging service.

At block 726, the messaging service may determine a value of the first module and the second module to the messaging service or a related social networking service. Block 726 may be carried out by the value model estimator 714 of FIG. 7A.

At block 728, the message service may determine a ranked order for the first module and the second module by combining the probability determined at block 724 with the value determined at block 726. For example, the probability of interaction may be multiplied by (or otherwise combined with) the value in order to determine a ranking score, and the modules may be ranked in the order of their respective ranking scores.

At block 730, the messaging service may determine intra-module rankings for the content of the first and second modules. This may involve arranging the content within the first module and/or the second module in an intra-module ranked order, as described in more detail in connection with FIG. 7C. Depending on whether certain content in a module is particularly relevant, then at block 732 the inter-module ranked order as determined at block 728 may be altered (e.g., to elevate a module having particularly relevant content).

At block 734, the first module and the second module may be displayed in the ranked order after a first subset of messages in the inbox interface.

FIG. 7C is a flowchart depicting an exemplary process performed by block 730, for determining an intra-module rank, in more detail. In general, the messaging service may be agnostic to the intra-module ranking, thus allowing each module to define its own intra-module ranking for content.

At block 738, the messaging service may identify a first content item and a second content item for a given module. The module may provide or define a location from which content items for the module may be retrieved.

At block 740, the messaging service may access ranking rules as provided by the module. Depending on the content, for example, the module may designate different criteria to be applied to rank the content. Exemplary criteria for ranking content within a module include a recency of the content, an importance of the content to a user, or an affinity for the content by the user, etc.

At block 742, the messaging service may determine a recency of the content, or any other information required by the criteria. The information about the criteria may be retrieved, for example, from a social networking service, the messaging service, a client device, or a remote location associated with the module.

At block 744, the system may determine a user affinity for the content items. The user affinity may represent a user affinity score 746 that indicates a likelihood that the inbox owner will enjoy the content. Alternatively or in addition, the user affinity may represent an associate affinity score 748 that indicates a likelihood that associates of the inbox owner (e.g., the inbox owner's friends through a social networking service or contacts through the messaging service) will enjoy the content.

At block 750, the messaging service may rank the first and second content items based on the affinity score(s) determined at block 744. Optionally, if one or more of the affinity scores exceeds a predetermined threshold (e.g., indicating that a content item is particularly relevant), then at block 752 the messaging service may flag the module containing the content for adjustment in the inter-module rankings.

At block 756, the messaging service may display the first and second content items within the module in the ranked order.

Messaging System Overview

Figure 8C:
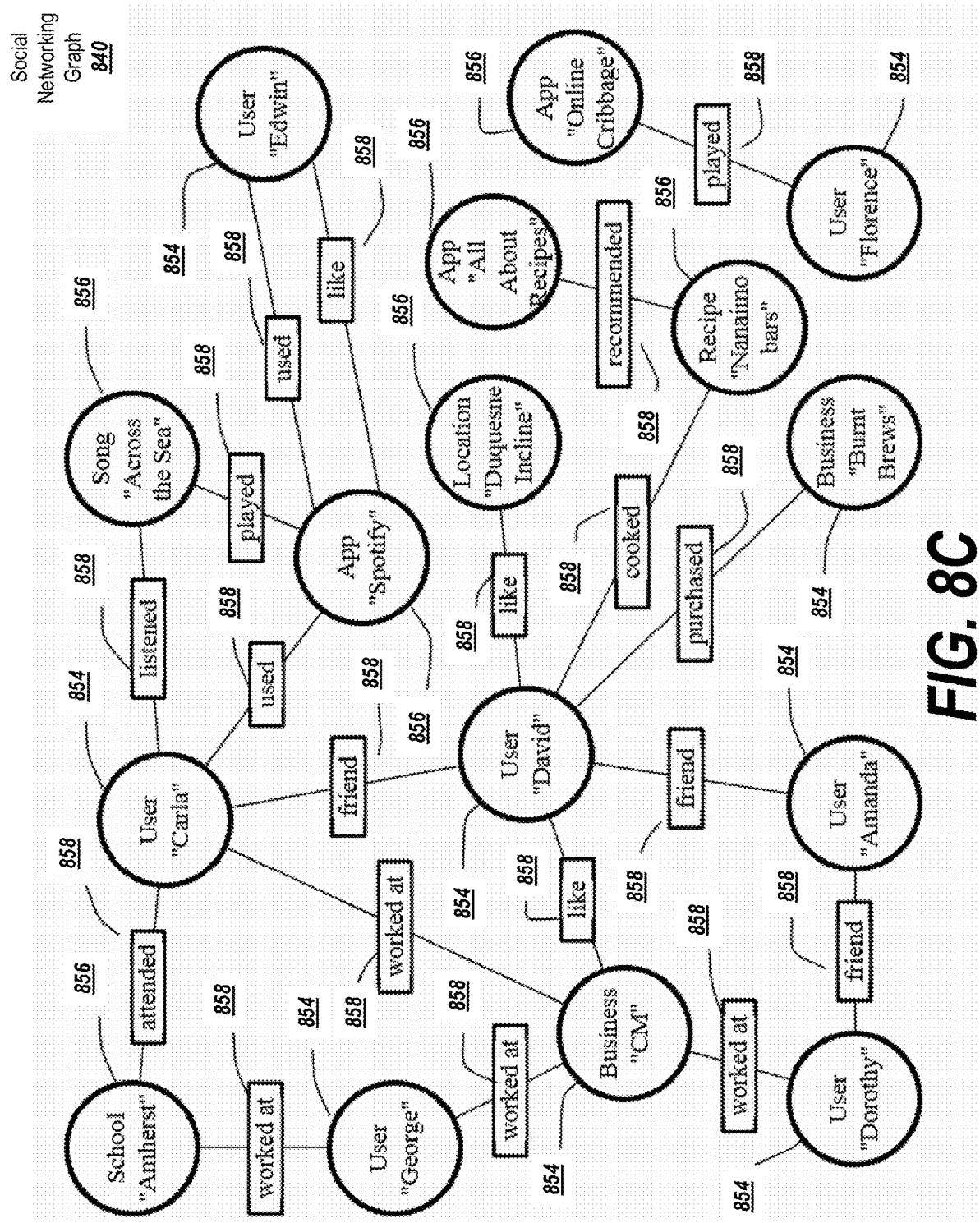
FIG. 8C depicts the social networking graph of FIGS. 8A-8B in more detail.

These examples may be implemented by a messaging system that is provided either locally, at a client device, or remotely (e.g., at a remote server). FIGS. 8A-8C depict various examples of messaging systems, and are discussed in more detail below.

FIG. 8A depicts an exemplary centralized messaging system 800, in which functionality for organizing messages asynchronously and/or using threads is integrated into a messaging server. The centralized system 800 may implement some or all of the structure and/or operations of a messaging service in a single computing entity, such as entirely within a single centralized server device 826.

The messaging system 800 may include a computer-implemented system having software applications that include one or more components. Although the messaging system 800 shown in FIG. 8A has a limited number of elements in a certain topology, the messaging system 800 may include more or fewer elements in alternate topologies.

A messaging service 800 may be generally arranged to receive, store, and deliver messages. The messaging service 800 may store messages while messaging clients 820, such as may execute on client devices 810, are offline and deliver the messages once the messaging clients are available.

A client device 810 may transmit messages addressed to a recipient user, user account, or other identifier resolving to a receiving client device 810. In exemplary embodiments, each of the client devices 810 and their respective messaging clients 820 are associated with a particular user or users of the messaging service 800. In some embodiments, the client devices 810 may be cellular devices such as smartphones and may be identified to the messaging service 800 based on a phone number associated with each of the client devices 810. In some embodiments, each messaging client may be associated with a user account registered with the messaging service 800. In general, each messaging client may be addressed through various techniques for the reception of messages. While in some embodiments the client devices 810 may be cellular devices, in other embodiments one or more of the client devices 810 may be personal computers, tablet devices, any other form of computing device.

The client 810 may include one or more input devices 812 and one or more output devices 818. The input devices 812 may include, for example, microphones, keyboards, cameras, electronic pens, touch screens, and other devices for receiving inputs including message data, requests, commands, user interface interactions, selections, and other types of input. The output devices 818 may include a speaker, a display device such as a monitor or touch screen, and other devices for presenting an interface to the messaging system 800.

The client 810 may include a memory 819, which may be a non-transitory computer readable storage medium, such as one or a combination of a hard drive, solid state drive, flash storage, read only memory, or random access memory. The memory 819 may a representation of an input 814 and/or a representation of an output 816, as well as one or more applications. For example, the memory 819 may store a messaging client 820 and/or a social networking client that allows a user to interact with a social networking service.

The input 814 may be textual, such as in the case where the input device 212 is a keyboard. Alternatively, the input 814 may be an audio recording, such as in the case where the input device 812 is a microphone. Accordingly, the input 814 may be subjected to automatic speech recognition (ASR) logic in order to transform the audio recording to text that is processable by the messaging system 800. The ASR logic may be located at the client device 810 (so that the audio recording is processed locally by the client 810 and corresponding text is transmitted to the messaging server 826), or may be located remotely at the messaging server 826 (in which case, the audio recording may be transmitted to the messaging server 826 and the messaging server 826 may process the audio into text). Other combinations are also possible—for example, if the input device 812 is a touch pad or electronic pen, the input 814 may be in the form of handwriting, which may be subjected to handwriting or optical character recognition analysis logic in order to transform the input 812 into processable text.

The client 810 may be provided with a network interface 822 for communicating with a network 824, such as the Internet. The network interface 822 may transmit the input 812 in a format and/or using a protocol compatible with the network 824 and may receive a corresponding output 816 from the network 824.

The network interface 822 may communicate through the network 824 to a messaging server 826. The messaging server 826 may be operative to receive, store, and forward messages between messaging clients.

The messaging server 826 may include a network interface 822, messaging preferences 828, and messaging inbox logic 830. The messaging preferences 828 may include one or more privacy settings for one or more users and/or message threads. For example, the messaging preferences 828 may include a setting that indicates whether to display messages synchronously or asynchronously. Furthermore, the messaging preferences 828 may include one or more settings, including default settings, for the logic described herein.

The messaging inbox logic 830 may include the logic for generating and maintaining a modular inbox as described above. For example, the messaging inbox logic 830 may include module logic 832 that is operable to generate modules for the inbox and manage interactions with the modules. The module logic 832 may include, for example, logic similar to that described in connection with FIGS. 3, 4G, 5D, and 6. The messaging inbox logic 830 may further include ranking logic 834 that is operable to perform inter-module and intra-module ranking, such as the logic described in connection with FIGS. 7B-7C.

The network interface 822 of the client 810 and/or the messaging server 826 may also be used to communicate through the network 824 with a social networking server 836. The social networking server 836 may include or may interact with a social networking graph 838 that defines connections in a social network. Furthermore, the messaging server 826 may connect to the social networking server 836 for various purposes, such as retrieving connection information, messaging history, event details, etc. from the social network.

A user of the client 810 may be an individual (human user), an entity (e.g., an enterprise, business, or third-party application), or a group (e.g., of individuals or entities) that interacts or communicates with or over the social networking server 836. The social-networking server 836 may be a network-addressable computing system hosting an online social network. The social networking server 836 may generate, store, receive, and send social-networking data, such as, for example, user-profile data, concept-profile data, social-graph information, or other suitable data related to the online social network. The social networking server 836 may be accessed by the other components of the network environment either directly or via the network 824.

The social networking server 836 may include an authorization server (or other suitable component(s)) that allows users to opt in to or opt out of having their actions logged by social-networking server 836 or shared with other systems (e.g., third-party systems, such as the messaging server 826), for example, by setting appropriate privacy settings. A privacy setting of a user may determine what information associated with the user may be logged, how information associated with the user may be logged, when information associated with the user may be logged, who may log information associated with the user, whom information associated with the user may be shared with, and for what purposes information associated with the user may be logged or shared. Authorization servers may be used to enforce one or more privacy settings of the users of social-networking server 836 through blocking, data hashing, anonymization, or other suitable techniques as appropriate.

More specifically, one or more of the content objects of the online social network may be associated with a privacy setting. The privacy settings (or "access settings") for an object may be stored in any suitable manner, such as, for example, in association with the object, in an index on an authorization server, in another suitable manner, or any combination thereof. A privacy setting of an object may specify how the object (or particular information associated with an object) can be accessed (e.g., viewed or shared) using the online social network. Where the privacy settings for an object allow a particular user to access that object, the object may be described as being "visible" with respect to that user. As an example and not by way of limitation, a user of the online social network may specify privacy settings for a user-profile page identify a set of users that may access the work experience information on the user-profile page, thus excluding other users from accessing the information. In particular embodiments, the privacy settings may specify a "blocked list" of users that should not be allowed to access certain information associated with the object. In other words, the blocked list may specify one or more users or entities for which an object is not visible. As an example and not by way of limitation, a user may specify a set of users that may not access photos albums associated with the user, thus excluding those users from accessing the photo albums (while also possibly allowing certain users not within the set of users to access the photo albums).

In particular embodiments, privacy settings may be associated with particular elements of the social networking graph 838. Privacy settings of a social-graph element, such as a node or an edge, may specify how the social-graph element, information associated with the social-graph element, or content objects associated with the social-graph element can be accessed using the online social network. As an example and not by way of limitation, a particular concept node corresponding to a particular photo may have a privacy setting specifying that the photo may only be accessed by users tagged in the photo and their friends. In particular embodiments, privacy settings may allow users to opt in or opt out of having their actions logged by social networking server 836 or shared with other systems. In particular embodiments, the privacy settings associated with an object may specify any suitable granularity of permitted access or denial of access. As an example and not by way of limitation, access or denial of access may be specified for particular users (e.g., only me, my roommates, and my boss), users within a particular degrees-of-separation (e.g., friends, or friends-of-friends), user groups (e.g., the gaming club, my family), user networks (e.g., employees of particular employers, students or alumni of particular university), all users ("public"), no users ("private"), users of third-party systems, particular applications (e.g., third-party applications, external websites), other suitable users or entities, or any combination thereof. Although this disclosure describes using particular privacy settings in a particular manner, this disclosure contemplates using any suitable privacy settings in any suitable manner.

In response to a request from a user (or other entity) for a particular object stored in a data store, the social networking server 836 may send a request to the data store for the object. The request may identify the user associated with the request. The requested data object may only be sent to the user (or a client system 810 of the user) if the authorization server determines that the user is authorized to access the object based on the privacy settings associated with the object. If the requesting user is not authorized to access the object, the authorization server may prevent the requested object from being retrieved from the data store, or may prevent the requested object from be sent to the user. In the search query context, an object may only be generated as a search result if the querying user is authorized to access the object. In other words, the object must have a visibility that is visible to the querying user. If the object has a visibility that is not visible to the user, the object may be excluded from the search results.

In some embodiments, targeting criteria may be used to identify users of the social network for various purposes. Targeting criteria used to identify and target users may include explicit, stated user interests on social-networking server 836 or explicit connections of a user to a node, object, entity, brand, or page on social networking server 836. In addition, or as an alternative, such targeting criteria may include implicit or inferred user interests or connections (which may include analyzing a user's history, demographic, social or other activities, friends' social or other activities, subscriptions, or any of the preceding of other users similar to the user (based, e.g., on shared interests, connections, or events)). Particular embodiments may utilize platform targeting, which may involve platform and "like" impression data; contextual signals (e.g., "Who is viewing now or has viewed recently the page for COCA-COLA?"); light-weight connections (e.g., "check-ins"); connection lookalikes; fans; extracted keywords; EMU advertising; inferential advertising; coefficients, affinities, or other social-graph information; friends-of-friends connections; pinning or boosting; deals; polls; household income, social clusters or groups; products detected in images or other media; social- or open-graph edge types; geo-prediction; views of profile or pages; status updates or other user posts (analysis of which may involve natural-language processing or keyword extraction); events information; or collaborative filtering. Identifying and targeting users may also implicate privacy settings (such as user opt-outs), data hashing, or data anonymization, as appropriate.

The centralized embodiment depicted in FIG. 8A may be well-suited to deployment as a new system or as an upgrade to an existing system, because the logic for pivoting to a group conversation (e.g., the logic of the account identifier 832 and/or the logic of the account notifier 834) are incorporated into the messaging server 826. In contrast, FIG. 8B depicts an exemplary distributed messaging system 880, in which functionality for recognizing productive intent and generating a list of suggested recipients is distributed and remotely accessible from the messaging server. Examples of a distributed system 880 include a client-server architecture, a 3-tier architecture, an N-tier architecture, a tightly-coupled or clustered architecture, a peer-to-peer architecture, a master-slave architecture, a shared database architecture, and other types of distributed systems.

Many of the components depicted in FIG. 8B are identical to those in FIG. 8A, and a description of these elements is not repeated here for the sake of brevity. The primary difference between the centralized embodiment and the distributed embodiment is the addition of a separate threading server 882, which hosts the thread creation component 832 and the thread display component 834. The threading server 882 may be distinct from the messaging server 826 but may communicate with the messaging server 826, either directly or through the network 824, to provide the functionality of the account identifier 832 and the account notifier 834 to the messaging server 826.

The embodiment depicted in FIG. 8B may be particularly well suited to allow exemplary embodiments to be deployed alongside existing messaging systems, for example when it is difficult or undesirable to replace an existing messaging server. Additionally, in some cases the messaging server 826 may have limited resources (e.g. processing or memory resources) that limit or preclude the addition of the additional pivot functionality. In such situations, the capabilities described herein may still be provided through the separate pivot server 882.

FIG. 8C illustrates an example of a social networking graph 838. In exemplary embodiments, a social networking service may store one or more social graphs 838 in one or more data stores as a social graph data structure via the social networking service.

The social graph 838 may include multiple nodes, such as user nodes 854 and concept nodes 856. The social graph 838 may furthermore include edges 858 connecting the nodes. The nodes and edges of social graph 838 may be stored as data objects, for example, in a data store (such as a social-graph database). Such a data store may include one or more searchable or queryable indexes of nodes or edges of social graph 838.

The social graph 838 may be accessed by a social-networking server 826, client system 810, third-party system, or any other approved system or device for suitable applications.

A user node 854 may correspond to a user of the social-networking system. A user may be an individual (human user), an entity (e.g., an enterprise, business, or third-party application), or a group (e.g., of individuals or entities) that interacts or communicates with or over the social-networking system. In exemplary embodiments, when a user registers for an account with the social-networking system, the social-networking system may create a user node 854 corresponding to the user, and store the user node 854 in one or more data stores. Users and user nodes 854 described herein may, where appropriate, refer to registered users and user nodes 854 associated with registered users. In addition or as an alternative, users and user nodes 854 described herein may, where appropriate, refer to users that have not registered with the social-networking system. In particular embodiments, a user node 854 may be associated with information provided by a user or information gathered by various systems, including the social-networking system. As an example and not by way of limitation, a user may provide their name, profile picture, contact information, birth date, sex, marital status, family status, employment, education background, preferences, interests, or other demographic information. In particular embodiments, a user node 854 may be associated with one or more data objects corresponding to information associated with a user. In particular embodiments, a user node 854 may correspond to one or more webpages. A user node 854 may be associated with a unique user identifier for the user in the social-networking system.

In particular embodiments, a concept node 856 may correspond to a concept. As an example and not by way of limitation, a concept may correspond to a place (such as, for example, a movie theater, restaurant, landmark, or city); a website (such as, for example, a website associated with the social-network service or a third-party website associated with a web-application server); an entity (such as, for example, a person, business, group, sports team, or celebrity); a resource (such as, for example, an audio file, video file, digital photo, text file, structured document, or application) which may be located within the social-networking system or on an external server, such as a web-application server; real or intellectual property (such as, for example, a sculpture, painting, movie, game, song, idea, photograph, or written work); a game; an activity; an idea or theory; another suitable concept; or two or more such concepts. A concept node 556 may be associated with information of a concept provided by a user or information gathered by various systems, including the social-networking system. As an example and not by way of limitation, information of a concept may include a name or a title; one or more images (e.g., an image of the cover page of a book); a location (e.g., an address or a geographical location); a website (which may be associated with a URL); contact information (e.g., a phone number or an email address); other suitable concept information; or any suitable combination of such information. In particular embodiments, a concept node 856 may be associated with one or more data objects corresponding to information associated with concept node 856. In particular embodiments, a concept node 856 may correspond to one or more webpages.

In particular embodiments, a node in social graph 838 may represent or be represented by a webpage (which may be referred to as a "profile page"). Profile pages may be hosted by or accessible to the social-networking system. Profile pages may also be hosted on third-party websites associated with a third-party server. As an example and not by way of limitation, a profile page corresponding to a particular external webpage may be the particular external webpage and the profile page may correspond to a particular concept node 856. Profile pages may be viewable by all or a selected subset of other users. As an example and not by way of limitation, a user node 854 may have a corresponding user-profile page in which the corresponding user may add content, make declarations, or otherwise express himself or herself. A business page may comprise a user-profile page for a commerce entity. As another example and not by way of limitation, a concept node 856 may have a corresponding concept-profile page in which one or more users may add content, make declarations, or express themselves, particularly in relation to the concept corresponding to concept node 856.

In particular embodiments, a concept node 856 may represent a third-party webpage or resource hosted by a third-party system. The third-party webpage or resource may include, among other elements, content, a selectable or other icon, or other inter-actable object (which may be implemented, for example, in JavaScript, AJAX, or PHP codes) representing an action or activity. As an example and not by way of limitation, a third-party webpage may include a selectable icon such as "like," "check in," "eat," "recommend," or another suitable action or activity. A user viewing the third-party webpage may perform an action by selecting one of the icons (e.g., "eat"), causing a client system to send to the social-networking system a message indicating the user's action. In response to the message, the social-networking system may create an edge (e.g., an "eat" edge) between a user node 854 corresponding to the user and a concept node 856 corresponding to the third-party webpage or resource and store edge 858 in one or more data stores.

In particular embodiments, a pair of nodes in social graph 838 may be connected to each other by one or more edges 858. An edge 858 connecting a pair of nodes may represent a relationship between the pair of nodes. In particular embodiments, an edge 858 may include or represent one or more data objects or attributes corresponding to the relationship between a pair of nodes. As an example and not by way of limitation, a first user may indicate that a second user is a "friend" of the first user. In response to this indication, the social-networking system may send a "friend request" to the second user. If the second user confirms the "friend request," the social-networking system may create an edge 858 connecting the first user's user node 854 to the second user's user node 854 in social graph 838 and store edge 858 as social-graph information in one or more data stores. In the example of FIG. 8C, social graph 838 includes an edge 858 indicating a friend relation between user nodes 854 of user "Amanda" and user "Dorothy." Although this disclosure describes or illustrates particular edges 858 with particular attributes connecting particular user nodes 854, this disclosure contemplates any suitable edges 858 with any suitable attributes connecting user nodes 854. As an example and not by way of limitation, an edge 858 may represent a friendship, family relationship, business or employment relationship, fan relationship, follower relationship, visitor relationship, subscriber relationship, superior/subordinate relationship, reciprocal relationship, non-reciprocal relationship, another suitable type of relationship, or two or more such relationships. Moreover, although this disclosure generally describes nodes as being connected, this disclosure also describes users or concepts as being connected. Herein, references to users or concepts being connected may, where appropriate, refer to the nodes corresponding to those users or concepts being connected in social graph 838 by one or more edges 858.

In particular embodiments, an edge 858 between a user node 854 and a concept node 856 may represent a particular action or activity performed by a user associated with user node 854 toward a concept associated with a concept node 856. As an example and not by way of limitation, as illustrated in FIG. 8C, a user may "like," "attended," "played," "listened," "cooked," "worked at," or "watched" a concept, each of which may correspond to an edge type or subtype. A concept-profile page corresponding to a concept node 856 may include, for example, a selectable "check in" icon (such as, for example, a clickable "check in" icon) or a selectable "add to favorites" icon. Similarly, after a user clicks these icons, the social-networking system may create a "favorite" edge or a "check in" edge in response to a user's action corresponding to a respective action. As another example and not by way of limitation, a user (user "Carla") may listen to a particular song ("Across the Sea") using a particular application (SPOTIFY, which is an online music application). In this case, the social-networking system may create a "listened" edge 858 and a "used" edge (as illustrated in FIG. 8C) between user nodes 854 corresponding to the user and concept nodes 856 corresponding to the song and application to indicate that the user listened to the song and used the application. Moreover, the social-networking system may create a "played" edge 858 (as illustrated in FIG. 8C) between concept nodes 856 corresponding to the song and the application to indicate that the particular song was played by the particular application. In this case, "played" edge 858 corresponds to an action performed by an external application (SPOTIFY) on an external audio file (the song "Across the Sea"). Although this disclosure describes particular edges 858 with particular attributes connecting user nodes 854 and concept nodes 856, this disclosure contemplates any suitable edges 858 with any suitable attributes connecting user nodes 854 and concept nodes 856. Moreover, although this disclosure describes edges between a user node 854 and a concept node 856 representing a single relationship, this disclosure contemplates edges between a user node 854 and a concept node 856 representing one or more relationships. As an example and not by way of limitation, an edge 858 may represent both that a user likes and has used at a particular concept. Alternatively, another edge 858 may represent each type of relationship (or multiples of a single relationship) between a user node 854 and a concept node 856 (as illustrated in FIG. 8C between user node 854 for user "Edwin" and concept node 856 for "SPOTIFY").

In particular embodiments, the social-networking system may create an edge 858 between a user node 854 and a concept node 856 in social graph 838. As an example and not by way of limitation, a user viewing a concept-profile page (such as, for example, by using a web browser or a special-purpose application hosted by the user's client system) may indicate that he or she likes the concept represented by the concept node 856 by clicking or selecting a "Like" icon, which may cause the user's client system to send to the social-networking system a message indicating the user's liking of the concept associated with the concept-profile page. In response to the message, the social-networking system may create an edge 858 between user node 854 associated with the user and concept node 856, as illustrated by "like" edge 858 between the user and concept node 856. In particular embodiments, the social-networking system may store an edge 858 in one or more data stores. In particular embodiments, an edge 858 may be automatically formed by the social-networking system in response to a particular user action. As an example and not by way of limitation, if a first user uploads a picture, watches a movie, or listens to a song, an edge 858 may be formed between user node 854 corresponding to the first user and concept nodes 856 corresponding to those concepts. Although this disclosure describes forming particular edges 858 in particular manners, this disclosure contemplates forming any suitable edges 858 in any suitable manner.

The social graph 838 may further comprise a plurality of product nodes. Product nodes may represent particular products that may be associated with a particular business. A business may provide a product catalog to a consumer-to-business service and the consumer-to-business service may therefore represent each of the products within the product in the social graph 838 with each product being in a distinct product node. A product node may comprise information relating to the product, such as pricing information, descriptive information, manufacturer information, availability information, and other relevant information. For example, each of the items on a menu for a restaurant may be represented within the social graph 838 with a product node describing each of the items. A product node may be linked by an edge to the business providing the product. Where multiple businesses provide a product, each business may have a distinct product node associated with its providing of the product or may each link to the same product node. A product node may be linked by an edge to each user that has purchased, rated, owns, recommended, or viewed the product, with the edge describing the nature of the relationship (e.g., purchased, rated, owns, recommended, viewed, or other relationship). Each of the product nodes may be associated with a graph id and an associated merchant id by virtue of the linked merchant business. Products available from a business may therefore be communicated to a user by retrieving the available product nodes linked to the user node for the business within the social graph 838. The information for a product node may be manipulated by the social-networking system as a product object that encapsulates information regarding the referenced product.

As such, the social graph 838 may be used to infer shared interests, shared experiences, or other shared or common attributes of two or more users of a social-networking system. For instance, two or more users each having an edge to a common business, product, media item, institution, or other entity represented in the social graph 838 may indicate a shared relationship with that entity, which may be used to suggest customization of a use of a social-networking system, including a messaging system, for one or more users.

The embodiments described above may be performed by a messaging architecture, an example of which is next described with reference to FIG. 9.

Messaging Architecture

Figure 9:
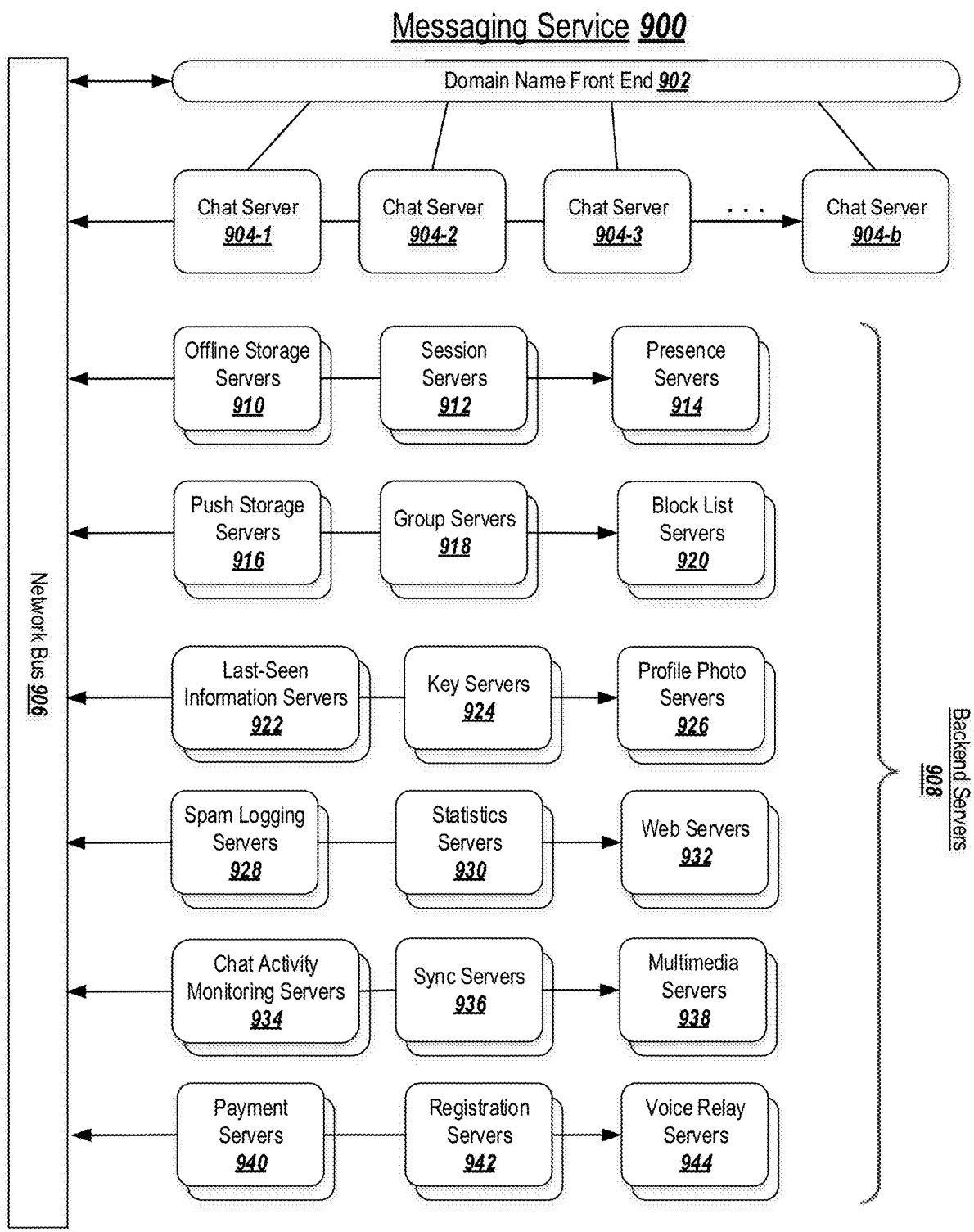
FIG. 9 is a block diagram depicting an example of a system for a messaging service.

FIG. 9 illustrates an embodiment of a plurality of servers implementing various functions of a messaging service 900. It will be appreciated that different distributions of work and functions may be used in various embodiments of a messaging service 900.

The messaging service 900 may comprise a domain name front end 902. The domain name front end 902 may be assigned one or more domain names associated with the messaging service 900 in a domain name system (DNS). The domain name front end 902 may receive incoming connections and distribute the connections to servers providing various messaging services.

The messaging service 902 may comprise one or more chat servers 904. The chat servers 904 may comprise front-end servers for receiving and transmitting user-to-user messaging updates such as chat messages. Incoming connections may be assigned to the chat servers 904 by the domain name front end 902 based on workload balancing.

The messaging service 900 may comprise backend servers 908. The backend servers 908 may perform specialized tasks in the support of the chat operations of the front-end chat servers 904. A plurality of different types of backend servers 908 may be used. It will be appreciated that the assignment of types of tasks to different backend serves 908 may vary in different embodiments. In some embodiments some of the back-end services provided by dedicated servers may be combined onto a single server or a set of servers each performing multiple tasks divided between different servers in the embodiment described herein. Similarly, in some embodiments tasks of some of dedicated back-end servers described herein may be divided between different servers of different server groups.

The messaging service 900 may comprise one or more offline storage servers 910. The one or more offline storage servers 910 may store messaging content for currently-offline messaging clients in hold for when the messaging clients reconnect.

The messaging service 900 may comprise one or more sessions servers 912. The one or more session servers 912 may maintain session state of connected messaging clients.

The messaging service 900 may comprise one or more presence servers 914. The one or more presence servers 914 may maintain presence information for the messaging service 900. Presence information may correspond to user-specific information indicating whether or not a given user has an online messaging client and is available for chatting, has an online messaging client but is currently away from it, does not have an online messaging client, and any other presence state.

The messaging service 900 may comprise one or more push storage servers 916. The one or more push storage servers 916 may cache push requests and transmit the push requests to messaging clients. Push requests may be used to wake messaging clients, to notify messaging clients that a messaging update is available, and to otherwise perform server-side-driven interactions with messaging clients.

The messaging service 900 may comprise one or more group servers 918. The one or more group servers 918 may maintain lists of groups, add users to groups, remove users from groups, and perform the reception, caching, and forwarding of group chat messages.

The messaging service 900 may comprise one or more block list servers 920. The one or more block list servers 920 may maintain user-specific block lists, the user-specific incoming-block lists indicating for each user the one or more other users that are forbidden from transmitting messages to that user. Alternatively or additionally, the one or more block list servers 920 may maintain user-specific outgoing-block lists indicating for each user the one or more other users that that user is forbidden from transmitting messages to. It will be appreciated that incoming-block lists and outgoing-block lists may be stored in combination in, for example, a database, with the incoming-block lists and outgoing-block lists representing different views of a same repository of block information.

The messaging service 900 may comprise one or more last seen information servers 922. The one or more last seen information servers 922 may receive, store, and maintain information indicating the last seen location, status, messaging client, and other elements of a user's last seen connection to the messaging service 900.

The messaging service 900 may comprise one or more key servers 924. The one or more key servers may host public keys for public/private key encrypted communication.

The messaging service 900 may comprise one or more profile photo servers 926. The one or more profile photo servers 926 may store and make available for retrieval profile photos for the plurality of users of the messaging service 900.

The messaging service 900 may comprise one or more spam logging servers 928. The one or more spam logging servers 928 may log known and suspected spam (e.g., unwanted messages, particularly those of a promotional nature). The one or more spam logging servers 928 may be operative to analyze messages to determine whether they are spam and to perform punitive measures, in some embodiments, against suspected spammers (users that send spam messages).

The messaging service 900 may comprise one or more statistics servers 930. The one or more statistics servers may compile and store statistics information related to the operation of the messaging service 900 and the behavior of the users of the messaging service 900.

The messaging service 900 may comprise one or more web servers 932. The one or more web servers 932 may engage in hypertext transport protocol (HTTP) and hypertext transport protocol secure (HTTPS) connections with web browsers.

The messaging service 900 may comprise one or more chat activity monitoring servers 934. The one or more chat activity monitoring servers 934 may monitor the chats of users to determine unauthorized or discouraged behavior by the users of the messaging service 900. The one or more chat activity monitoring servers 934 may work in cooperation with the spam logging servers 928 and block list servers 920, with the one or more chat activity monitoring servers 934 identifying spam or other discouraged behavior and providing spam information to the spam logging servers 928 and blocking information, where appropriate to the block list servers 920.

The messaging service 900 may comprise one or more sync servers 936. The one or more sync servers 936 may sync the messaging system 500 with contact information from a messaging client, such as an address book on a mobile phone, to determine contacts for a user in the messaging service 900.

The messaging service 900 may comprise one or more multimedia servers 938. The one or more multimedia servers may store multimedia (e.g., images, video, audio) in transit between messaging clients, multimedia cached for offline endpoints, and may perform transcoding of multimedia.

The messaging service 900 may comprise one or more payment servers 940. The one or more payment servers 940 may process payments from users. The one or more payment servers 940 may connect to external third-party servers for the performance of payments.

The messaging service 900 may comprise one or more registration servers 942. The one or more registration servers 942 may register new users of the messaging service 900.

The messaging service 900 may comprise one or more voice relay servers 944. The one or more voice relay servers 944 may relay voice-over-internet-protocol (VoIP) voice communication between messaging clients for the performance of VoIP calls.

Figure 10:
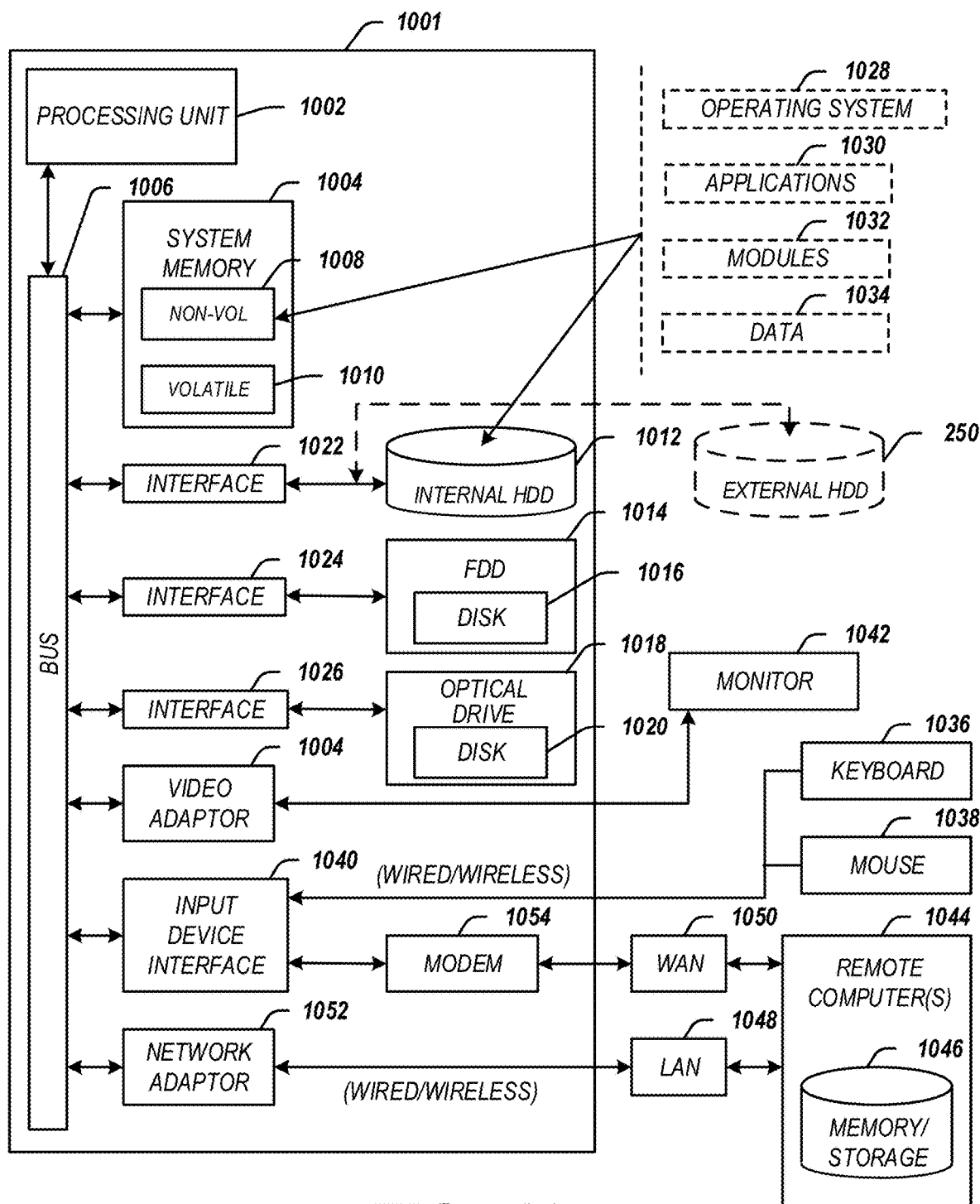
FIG. 10 is a block diagram illustrating an exemplary computing device suitable for use with exemplary embodiments.

The above-described methods may be embodied as instructions on a computer readable medium or as part of a computing architecture. FIG. 10 illustrates an embodiment of an exemplary computing architecture 1000 suitable for implementing various embodiments as previously described. In one embodiment, the computing architecture 1000 may comprise or be implemented as part of an electronic device, such as a computer 1001. The embodiments are not limited in this context.

As used in this application, the terms "system" and "component" are intended to refer to a computer-related entity, either hardware, a combination of hardware and software, software, or software in execution, examples of which are provided by the exemplary computing architecture 1000. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1000 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1000.

As shown in FIG. 10, the computing architecture 1000 comprises a processing unit 1002, a system memory 1004 and a system bus 1006. The processing unit 1002 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1002.

The system bus 1006 provides an interface for system components including, but not limited to, the system memory 1004 to the processing unit 1002. The system bus 1006 can be any of several types of bus structure that may further interconnect to a memory bus (with or without a memory controller), a peripheral bus, and a local bus using any of a variety of commercially available bus architectures. Interface adapters may connect to the system bus 1006 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The computing architecture 1000 may comprise or implement various articles of manufacture. An article of manufacture may comprise a computer-readable storage medium to store logic. Examples of a computer-readable storage medium may include any tangible media capable of storing electronic data, including volatile memory or non-volatile memory, removable or non-removable memory, erasable or non-erasable memory, writeable or re-writeable memory, and so forth. Examples of logic may include executable computer program instructions implemented using any suitable type of code, such as source code, compiled code, interpreted code, executable code, static code, dynamic code, object-oriented code, visual code, and the like. Embodiments may also be at least partly implemented as instructions contained in or on a non-transitory computer-readable medium, which may be read and executed by one or more processors to enable performance of the operations described herein.

The system memory 1004 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 10, the system memory 1004 can include non-volatile memory 1008 and/or volatile memory 1010. A basic input/output system (BIOS) can be stored in the non-volatile memory 1008.

The computing architecture 1000 may include various types of computer-readable storage media in the form of one or more lower speed memory units, including an internal (or external) hard disk drive (HDD) 1012, a magnetic floppy disk drive (FDD) 1014 to read from or write to a removable magnetic disk 1016, and an optical disk drive 1018 to read from or write to a removable optical disk 1020 (e.g., a CD-ROM or DVD). The HDD 1012, FDD 1014 and optical disk drive 1020 can be connected to the system bus 1006 by an HDD interface 1022, an FDD interface 1024 and an optical drive interface 1026, respectively. The HDD interface 1022 for external drive implementations can include at least one or both of Universal Serial Bus (USB) and IEEE 694 interface technologies.

The drives and associated computer-readable media provide volatile and/or nonvolatile storage of data, data structures, computer-executable instructions, and so forth. For example, a number of program modules can be stored in the drives and memory units 1008, 1012, including an operating system 1028, one or more application programs 1030, other program modules 1032, and program data 1034. In one embodiment, the one or more application programs 1030, other program modules 1032, and program data 1034 can include, for example, the various applications and/or components of the messaging system 500.

A user can enter commands and information into the computer 1001 through one or more wire/wireless input devices, for example, a keyboard 1036 and a pointing device, such as a mouse 1038. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1002 through an input device interface 1040 that is coupled to the system bus 1006, but can be connected by other interfaces such as a parallel port, IEEE 694 serial port, a game port, a USB port, an IR interface, and so forth.

A monitor 1042 or other type of display device is also connected to the system bus 1006 via an interface, such as a video adaptor 1044. The monitor 1042 may be internal or external to the computer 1001. In addition to the monitor 1042, a computer typically includes other peripheral output devices, such as speakers, printers, and so forth.

The computer 1001 may operate in a networked environment using logical connections via wire and/or wireless communications to one or more remote computers, such as a remote computer 1044. The remote computer 1044 can be a workstation, a server computer, a router, a personal computer, portable computer, microprocessor-based entertainment appliance, a peer device or other common network node, and typically includes many or all of the elements described relative to the computer 1001, although, for purposes of brevity, only a memory/storage device 1046 is illustrated. The logical connections depicted include wire/wireless connectivity to a local area network (LAN) 1048 and/or larger networks, for example, a wide area network (WAN) 1050. Such LAN and WAN networking environments are commonplace in offices and companies, and facilitate enterprise-wide computer networks, such as intranets, all of which may connect to a global communications network, for example, the Internet.

When used in a LAN networking environment, the computer 1001 is connected to the LAN 1048 through a wire and/or wireless communication network interface or adaptor 1052. The adaptor 1052 can facilitate wire and/or wireless communications to the LAN 1048, which may also include a wireless access point disposed thereon for communicating with the wireless functionality of the adaptor 1052.

When used in a WAN networking environment, the computer 1001 can include a modem 1054, or is connected to a communications server on the WAN 1050, or has other means for establishing communications over the WAN 1050, such as by way of the Internet. The modem 1054, which can be internal or external and a wire and/or wireless device, connects to the system bus 1006 via the input device interface 1040. In a networked environment, program modules depicted relative to the computer 1001, or portions thereof, can be stored in the remote memory/storage device 1046. It will be appreciated that the network connections shown are exemplary and other means of establishing a communications link between the computers can be used.

The computer 1001 is operable to communicate with wire and wireless devices or entities using the IEEE 802 family of standards, such as wireless devices operatively disposed in wireless communication (e.g., IEEE 802.13 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.13x (a, b, g, n, etc.) to provide secure, reliable, fast wireless connectivity. A Wi-Fi network can be used to connect computers to each other, to the Internet, and to wire networks (which use IEEE 802.3-related media and functions).

Figure 11:
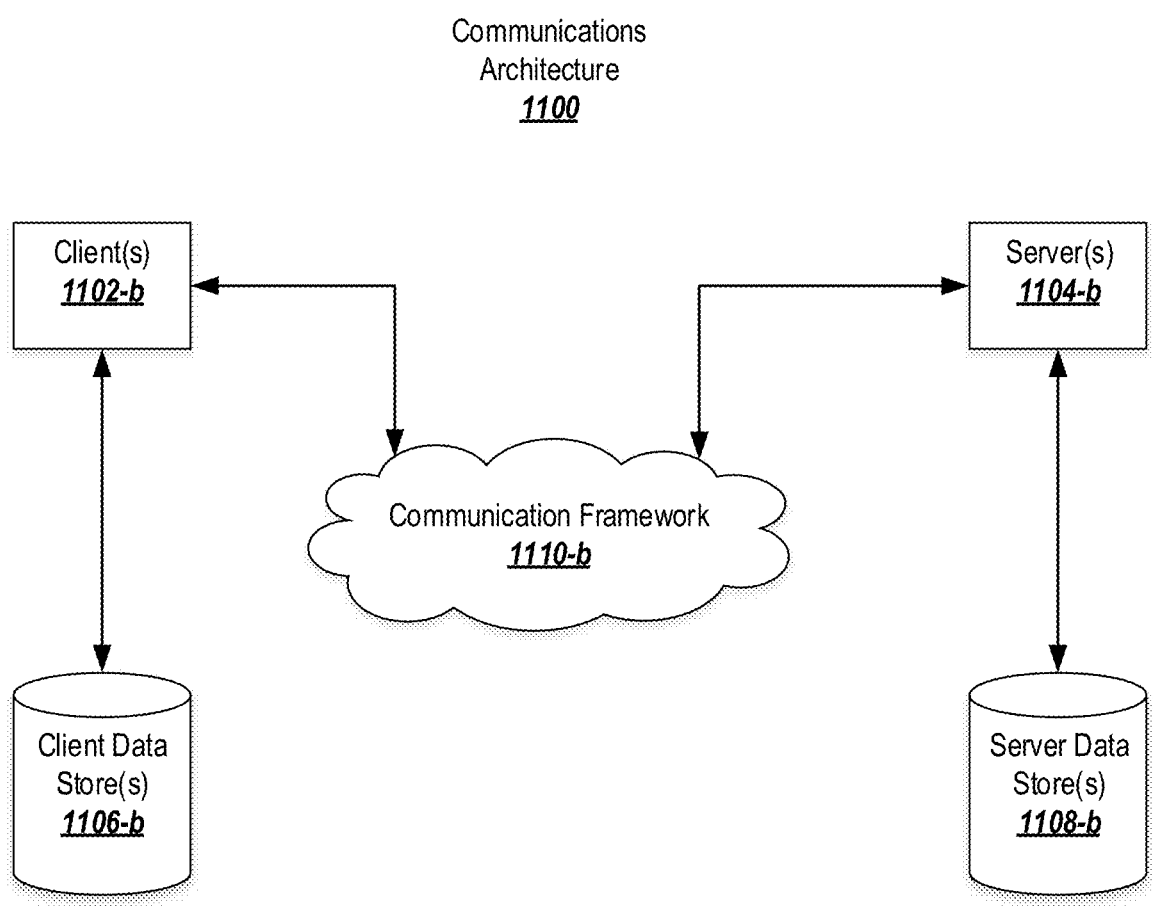
FIG. 11 depicts an exemplary communication architecture.

FIG. 11 is a block diagram depicting an exemplary communications architecture 1100 suitable for implementing various embodiments as previously described. The communications architecture 1100 includes various common communications elements, such as a transmitter, receiver, transceiver, radio, network interface, baseband processor, antenna, amplifiers, filters, power supplies, and so forth. The embodiments, however, are not limited to implementation by the communications architecture 1100.

As shown in FIG. 11, the communications architecture 1100 includes one or more clients 1102 and servers 1104. The clients 1102 may implement the client device 510. The servers 1104 may implement the server device 526. The clients 1102 and the servers 1104 are operatively connected to one or more respective client data stores 1106 and server data stores 1108 that can be employed to store information local to the respective clients 1102 and servers 1104, such as cookies and/or associated contextual information.

The clients 1102 and the servers 1104 may communicate information between each other using a communication framework 1110. The communications framework 1110 may implement any well-known communications techniques and protocols. The communications framework 1110 may be implemented as a packet-switched network (e.g., public networks such as the Internet, private networks such as an enterprise intranet, and so forth), a circuit-switched network (e.g., the public switched telephone network), or a combination of a packet-switched network and a circuit-switched network (with suitable gateways and translators).

The communications framework 1110 may implement various network interfaces arranged to accept, communicate, and connect to a communications network. A network interface may be regarded as a specialized form of an input output interface. Network interfaces may employ connection protocols including without limitation direct connect, Ethernet (e.g., thick, thin, twisted pair 10/100/1000 Base T, and the like), token ring, wireless network interfaces, cellular network interfaces, IEEE 802.11a-x network interfaces, IEEE 802.16 network interfaces, IEEE 802.20 network interfaces, and the like. Further, multiple network interfaces may be used to engage with various communications network types. For example, multiple network interfaces may be employed to allow for the communication over broadcast, multicast, and unicast networks. Should processing requirements dictate a greater amount speed and capacity, distributed network controller architectures may similarly be employed to pool, load balance, and otherwise increase the communicative bandwidth required by clients 1102 and the servers 1104. A communications network may be any one and the combination of wired and/or wireless networks including without limitation a direct interconnection, a secured custom connection, a private network (e.g., an enterprise intranet), a public network (e.g., the Internet), a Personal Area Network (PAN), a Local Area Network (LAN), a Metropolitan Area Network (MAN), an Operating Missions as Nodes on the Internet (OMNI), a Wide Area Network (WAN), a wireless network, a cellular network, and other communications networks.

Figure 12:
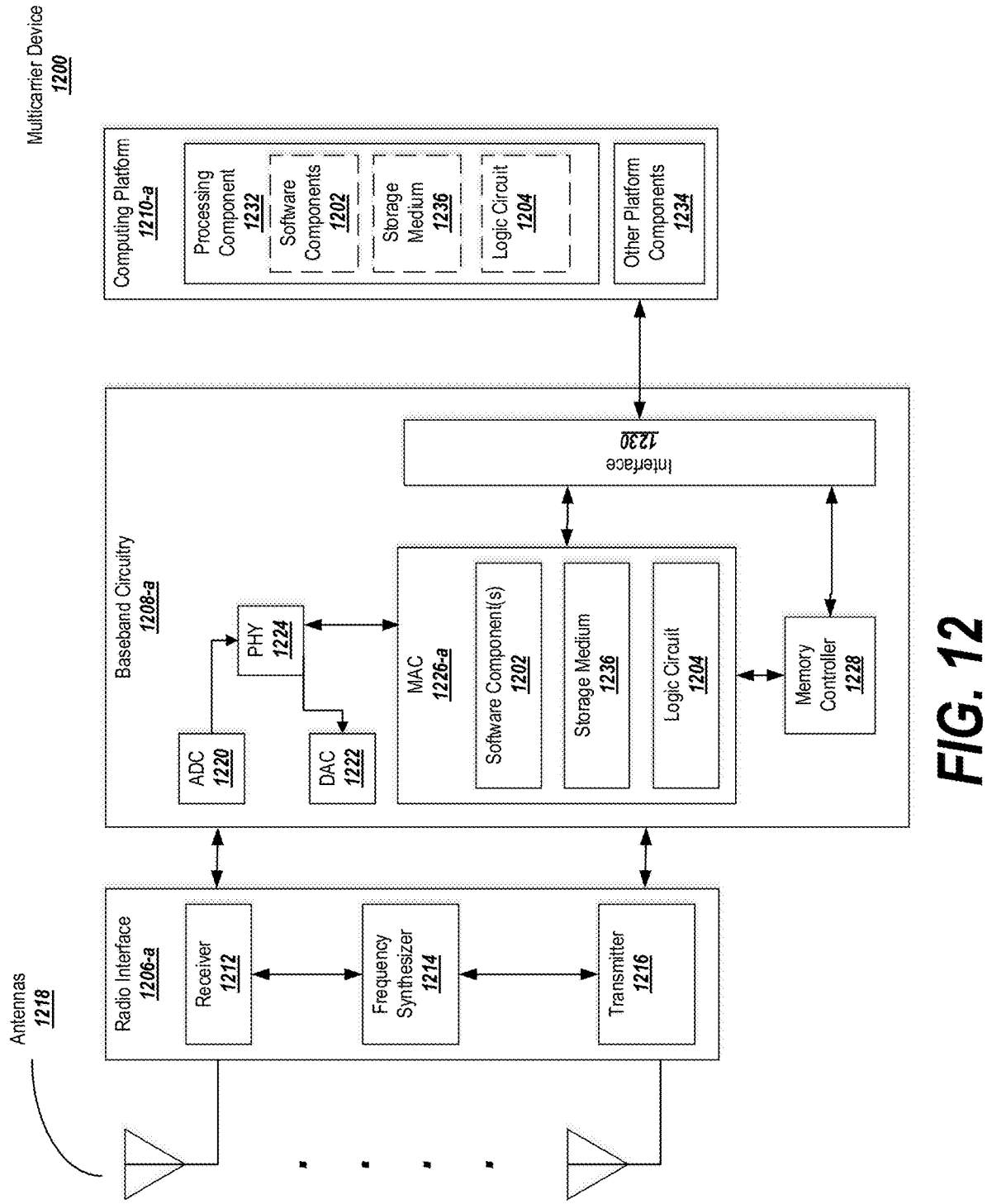
FIG. 12 is a block diagram depicting an exemplary multicarrier communications device.

FIG. 12 illustrates an embodiment of a device 1200 for use in a multicarrier OFDM system, such as the messaging system 500. The device 1200 may implement, for example, software components 1202 as described with reference to the messaging component logic 600, the intent determination logic 700, and the group selection logic 800. The device 1200 may also implement a logic circuit 1204. The logic circuit 1204 may include physical circuits to perform operations described for the messaging system 500. As shown in FIG. 12, device 1200 may include a radio interface 1206, baseband circuitry 1208, and a computing platform 1210, although embodiments are not limited to this configuration.

The device 1200 may implement some or all of the structure and/or operations for the messaging system 500 and/or logic circuit 1204 in a single computing entity, such as entirely within a single device. Alternatively, the device 1200 may distribute portions of the structure and/or operations for the messaging system 500 and/or logic circuit 1204 across multiple computing entities using a distributed system architecture, such as a client-server architecture, a 3-tier architecture, an N-tier architecture, a tightly-coupled or clustered architecture, a peer-to-peer architecture, a master-slave architecture, a shared database architecture, and other types of distributed systems. The embodiments are not limited in this context.

In one embodiment, the radio interface 1206 may include a component or combination of components adapted for transmitting and/or receiving single carrier or multi-carrier modulated signals (e.g., including complementary code keying (CCK) and/or orthogonal frequency division multiplexing (OFDM) symbols) although the embodiments are not limited to any specific over-the-air interface or modulation scheme. The radio interface 1206 may include, for example, a receiver 1212, a transmitter 1214 and/or a frequency synthesizer 1216. The radio interface 1206 may include bias controls, a crystal oscillator and/or one or more antennas 1218. In another embodiment, the radio interface 1206 may use external voltage-controlled oscillators (VCOs), surface acoustic wave filters, intermediate frequency (IF) filters and/or RF filters, as desired. Due to the variety of potential RF interface designs an expansive description thereof is omitted.

The baseband circuitry 1208 may communicate with the radio interface 1206 to process receive and/or transmit signals and may include, for example, an analog-to-digital converter 1220 for down converting received signals, and a digital-to-analog converter 1222 for up-converting signals for transmission. Further, the baseband circuitry 1208 may include a baseband or physical layer (PHY) processing circuit 1224 for PHY link layer processing of respective receive/transmit signals. The baseband circuitry 1208 may include, for example, a processing circuit 1226 for medium access control (MAC)/data link layer processing. The baseband circuitry 1208 may include a memory controller 1228 for communicating with the processing circuit 1226 and/or a computing platform 1210, for example, via one or more interfaces 1230.

In some embodiments, the PHY processing circuit 1224 may include a frame construction and/or detection module, in combination with additional circuitry such as a buffer memory, to construct and/or deconstruct communication frames, such as radio frames. Alternatively or in addition, the MAC processing circuit 1226 may share processing for certain of these functions or perform these processes independent of the PHY processing circuit 1224. In some embodiments, MAC and PHY processing may be integrated into a single circuit.

The computing platform 1210 may provide computing functionality for the device 1200. As shown, the computing platform 1210 may include a processing component 1232. In addition to, or alternatively of, the baseband circuitry 1208, the device 1200 may execute processing operations or logic for the messaging system 500 and logic circuit 1204 using the processing component 1232. The processing component 1232 (and/or the PHY 1224 and/or MAC 1226) may comprise various hardware elements, software elements, or a combination of both. Examples of hardware elements may include devices, logic devices, components, processors, microprocessors, circuits, processor circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints, as desired for a given implementation.

The computing platform 1210 may further include other platform components 1234. Other platform components 1234 include common computing elements, such as one or more processors, multi-core processors, co-processors, memory units, chipsets, controllers, peripherals, interfaces, oscillators, timing devices, video cards, audio cards, multimedia input/output (I/O) components (e.g., digital displays), power supplies, and so forth. Examples of memory units may include without limitation various types of computer readable and machine readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information.

The device 1200 may be, for example, an ultra-mobile device, a mobile device, a fixed device, a machine-to-machine (M2M) device, a personal digital assistant (PDA), a mobile computing device, a smart phone, a telephone, a digital telephone, a cellular telephone, user equipment, eBook readers, a handset, a one-way pager, a two-way pager, a messaging device, a computer, a personal computer (PC), a desktop computer, a laptop computer, a notebook computer, a netbook computer, a handheld computer, a tablet computer, a server, a server array or server farm, a web server, a network server, an Internet server, a work station, a mini-computer, a main frame computer, a supercomputer, a network appliance, a web appliance, a distributed computing system, multiprocessor systems, processor-based systems, consumer electronics, programmable consumer electronics, game devices, television, digital television, set top box, wireless access point, base station, node B, evolved node B (eNB), subscriber station, mobile subscriber center, radio network controller, router, hub, gateway, bridge, switch, machine, or combination thereof. Accordingly, functions and/or specific configurations of the device 1200 described herein, may be included or omitted in various embodiments of the device 1200, as suitably desired. In some embodiments, the device 1200 may be configured to be compatible with protocols and frequencies associated one or more of the 3GPP LTE Specifications and/or IEEE 1402.16 Standards for WMANs, and/or other broadband wireless networks, cited herein, although the embodiments are not limited in this respect.

Embodiments of device 1200 may be implemented using single input single output (SISO) architectures. However, certain implementations may include multiple antennas (e.g., antennas 1218) for transmission and/or reception using adaptive antenna techniques for beamforming or spatial division multiple access (SDMA) and/or using MIMO communication techniques.

The components and features of the device 1200 may be implemented using any combination of discrete circuitry, application specific integrated circuits (ASICs), logic gates and/or single chip architectures. Further, the features of the device 1200 may be implemented using microcontrollers, programmable logic arrays and/or microprocessors or any combination of the foregoing where suitably appropriate. It is noted that hardware, firmware and/or software elements may be collectively or individually referred to herein as "logic" or "circuit."

It will be appreciated that the exemplary device 1200 shown in the block diagram of FIG. 12 may represent one functionally descriptive example of many potential implementations. Accordingly, division, omission or inclusion of block functions depicted in the accompanying figures does not infer that the hardware components, circuits, software and/or elements for implementing these functions would be necessarily be divided, omitted, or included in embodiments.

At least one computer-readable storage medium 1236 may include instructions that, when executed, cause a system to perform any of the computer-implemented methods described herein.

General Notes on Terminology

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

The invention claimed is:

1. A method, comprising:
receiving, from a messaging service, a plurality of messages in an inbox of a messaging application on a client device; and
presenting an inbox interface of the messaging application, the inbox interface comprising:
a first portion displaying a first set of unread messages from the inbox;
a second portion displaying a plurality of functional modules providing services different from the message or message thread presentation features of the messaging application; and
a third portion displaying a second set of messages comprising remaining messages in the inbox not displayed in the first portion;
wherein content items having purely promotional content are displayed in an advertising-specific functional module and further wherein content items having a discount offer are displayed in non-advertising-specific functional modules.

2. The method of claim 1, further comprising:
detecting a location of the client device; and
selecting the promotional content based on a proximity of the client device to a source of the promotional content.

3. The method of claim 1, further comprising:
receiving a user interaction with the promotional content; and
displaying a user interface allowing the sending of the promotional content to one or more other client devices.

4. The method of claim 1, further comprising:
receiving a user interaction with the promotional content; and
sending a new message or thread to the inbox regarding the promotional content.

5. The method of claim 1, wherein the promotional content comprises a scannable code offering a discount when scanned at a retail location associated with the promotional content.

6. The method of claim 1, further comprising:
determining a user affinity of a user of the messaging application for a plurality of promotional contents;
ranking the plurality of promotional contents based on the user affinity; and
displaying higher-ranked promotional contents earlier within the functional module.

7. The method of claim 6, further comprising:
determining a ranking of a plurality of functional modules based on the rankings of promotional contents displayed within each functional module; and
displaying higher-ranked functional modules earlier in the second portion of the inbox.

8. A system comprising:
a processor; and
memory, coupled to the processor and storing software that, when executed by the processor, cause the system to:
receive, from a messaging service, a plurality of messages in an inbox of a messaging application on a client device; and
present an inbox interface of the messaging application for the messaging service, the inbox interface comprising:
a first portion displaying a first set of unread messages from the inbox;
a second portion displaying a plurality of functional modules providing services different from the message or message thread presentation features of the messaging application; and
a third portion displaying a second set of messages comprising remaining messages in the inbox not displayed in the first portion;
wherein content items having purely promotional content are displayed in an advertising-specific functional module and further wherein content items having a discount offer are displayed in non-advertising-specific functional modules.

9. The system of claim 8, the software further causing the system to:
detect a location of the client device; and
select the promotional content based on a proximity of the client device to a source of the promotional content.

10. The system of claim 8, the software further causing the system to:
receive a user interaction with the promotional content; and
display a user interface allowing the sending of the promotional content to one or more other client devices.

11. The system of claim 8, the software further causing the system to:
receive a user interaction with the promotional content; and
send a new message or thread to the inbox regarding the promotional content.

12. The system of claim 8, wherein the promotional content comprises a scannable code offering a discount when scanned at a retail location associated with the promotional content.

13. The system of claim 8, the software further causing the system to:
determine a user affinity for a plurality of promotional contents;
rank the plurality of promotional contents based on the user affinity; and
display higher-ranked promotional contents earlier within the functional module.

14. The system of claim 13, the software further causing the system to:
determine a ranking of a plurality of functional modules based on the ranking of promotional contents displayed within each functional module; and
display higher-ranked functional modules earlier in the second portion of the inbox.

15. A non-volatile, computer-readable storage medium containing software that, when executed by a processor, cause a system to:
receive, from a messaging service, a plurality of messages in an inbox of a messaging application on a client device; and present an inbox interface of the messaging application for the messaging service, the inbox interface comprising:

a first portion displaying a first set of unread messages from the inbox;

a second portion displaying a plurality of functional modules providing services different from the message or message thread presentation features of the messaging application; and a third portion displaying a second set of messages comprising remaining messages in the inbox not displayed in the first portion;

wherein content items having purely promotional content are displayed in an advertising-specific functional module and further wherein content items having a discount offer are displayed in non-advertising-specific functional modules.

16. The medium of claim 15, the software further causing the system to:

detect a location of the client device; and select the promotional content based on a proximity of the client device to a source of the promotional content.

17. The medium of claim 15, the software further causing the system to:

receive a user interaction with the promotional content; and display a user interface allowing the sending of the promotional content to one or more other client devices.

18. The medium of claim 15, the software further causing the system to:

receive a user interaction with the promotional content; and send a new message or thread to the inbox regarding the promotional content;

wherein the promotional content comprises a scannable code offering a discount when scanned at a retail location associated with the promotional content.

19. The medium of claim 15, the software further causing the system to:

determine a user affinity for a plurality of promotional contents;

rank the plurality of promotional contents based on the user affinity; and display higher-ranked promotional contents earlier within the functional module.

20. The medium of claim 19, the software further causing the system to:

determine a ranking of a plurality of functional modules based on the ranking of promotional contents displayed within each functional module; and display higher-ranked functional modules earlier in the second portion of the inbox.

* * * * *